United States Patent
Liang et al.

(10) Patent No.: US 12,426,782 B2
(45) Date of Patent: Sep. 30, 2025

(54) SYSTEMS AND TEMPORAL ALIGNMENT METHODS FOR EVALUATION OF GESTATIONAL AGE AND TIME TO DELIVERY

(71) Applicant: The Board of Trustees of the Leland Stanford Junior University, Stanford, CA (US)

(72) Inventors: Liang Liang, Whitefish Bay, WI (US); Rajanala Samyak, Stanford, CA (US); Robert Tibshirani, Palo Alto, CA (US); Trevor Hastie, Stanford, CA (US); Michael P. Snyder, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 742 days.

(21) Appl. No.: 17/454,044

(22) Filed: Nov. 8, 2021

(65) Prior Publication Data
US 2022/0142477 A1    May 12, 2022

Related U.S. Application Data

(60) Provisional application No. 63/110,872, filed on Nov. 6, 2020.

(51) Int. Cl.
*A61B 5/00* (2006.01)
*G16B 30/00* (2019.01)
*G16B 40/20* (2019.01)

(52) U.S. Cl.
CPC ............ *A61B 5/0011* (2013.01); *G16B 30/00* (2019.02); *G16B 40/20* (2019.02)

(58) Field of Classification Search
None
See application file for complete search history.

(56) References Cited

U.S. PATENT DOCUMENTS

| | | | |
|---|---|---|---|
| 5,045,694 | A | 9/1991 | Beavis et al. |
| 5,118,937 | A | 6/1992 | Hillenkamp et al. |
| 5,565,332 | A | 10/1996 | Hoogenboom et al. |

(Continued)

FOREIGN PATENT DOCUMENTS

| | | |
|---|---|---|
| AU | 2014227891 A1 | 10/2015 |
| AU | 2014228009 A1 | 10/2015 |

(Continued)

OTHER PUBLICATIONS

David L. Healy, Placental Endocrinology, 1987, Plenum Publishing Corporation, pp. 23-53. (Year: 1987).*

(Continued)

*Primary Examiner* — Kathryn Elizabeth Limbaugh
(74) *Attorney, Agent, or Firm* — KPPB LLP

(57) ABSTRACT

Methods to compute gestational age and time to delivery utilizing temporal alignment methods and applications thereof are described. Generally, systems utilize analyte measurements collected at one or more time points to determine a gestational age and time to delivery, which can be used as a basis to perform interventions and treat individuals. Computational models trained utilizing temporal alignment of analyte measurements can be used to determine gestational age and time to delivery.

17 Claims, 20 Drawing Sheets

(56) References Cited

U.S. PATENT DOCUMENTS

| | | | |
|---|---|---|---|
| 5,719,060 | A | 2/1998 | Hutchens et al. |
| 5,872,126 | A | 2/1999 | Cukierski et al. |
| 5,981,180 | A | 11/1999 | Chandler et al. |
| 6,225,047 | B1 | 5/2001 | Hutchens et al. |
| 6,524,793 | B1 | 2/2003 | Chandler et al. |
| 7,445,844 | B2 | 11/2008 | Chandler et al. |
| 2004/0266025 | A1 | 12/2004 | Hickok et al. |
| 2008/0188829 | A1 | 8/2008 | Creasy |
| 2012/0157422 | A1 | 6/2012 | Poston et al. |
| 2014/0141102 | A1 | 5/2014 | Garfield et al. |
| 2014/0194397 | A1 | 7/2014 | Henry |
| 2014/0287947 | A1 | 9/2014 | Boniface et al. |
| 2018/0296487 | A1 | 10/2018 | Saporito et al. |
| 2019/0000812 | A1 | 1/2019 | Page et al. |
| 2019/0046647 | A1 | 2/2019 | House et al. |
| 2020/0071761 | A1* | 3/2020 | Boniface ............... G01N 33/689 |
| 2021/0057039 | A1* | 2/2021 | Brohman ............ G01N 33/5076 |
| 2021/0398682 | A1 | 12/2021 | Liang et al. |
| 2022/0291243 | A1* | 9/2022 | Patil ........................ G16H 10/40 |
| 2022/0339176 | A1 | 10/2022 | Liang et al. |
| 2023/0298758 | A1 | 9/2023 | Liang et al. |
| 2024/0358719 | A1 | 10/2024 | Liang et al. |

FOREIGN PATENT DOCUMENTS

| | | |
|---|---|---|
| CN | 1250373 A | 4/2000 |
| CN | 101063678 A | 10/2007 |
| CN | 101094676 A | 12/2007 |
| CN | 101389964 A | 3/2009 |
| CN | 102884006 A | 1/2013 |
| CN | 106574919 A | 4/2017 |
| CN | 113396332 A | 9/2021 |
| CN | 114728013 A | 7/2022 |
| CN | 117202910 A | 12/2023 |
| CN | 113396332 B | 2/2025 |
| EP | 2149371 A1 | 2/2010 |
| EP | 3853613 A1 | 7/2021 |
| EP | 4034129 A1 | 8/2022 |
| EP | 4241285 A1 | 9/2023 |
| EP | 4313061 A1 | 2/2024 |
| HK | 40062939 A | 6/2022 |
| JP | 2004277312 A | 10/2004 |
| JP | 2010518058 A | 5/2010 |
| JP | 2011529485 A | 12/2011 |
| JP | 2016518589 A | 6/2016 |
| JP | 2022-517163 A | 3/2022 |
| JP | 2022548314 A | 11/2022 |
| JP | 2023110034 A | 8/2023 |
| JP | 2024511658 A | 3/2024 |
| WO | 1993003151 A1 | 2/1993 |
| WO | 1994013804 A1 | 6/1994 |
| WO | 1998034621 A1 | 8/1998 |
| WO | 2000067708 A2 | 11/2000 |
| WO | 2001015679 A2 | 3/2001 |
| WO | 2004071427 A2 | 8/2004 |
| WO | 2006047859 A1 | 5/2006 |
| WO | 2007049157 A2 | 5/2007 |
| WO | 2012058463 A2 | 5/2012 |
| WO | 2013144356 A1 | 10/2013 |
| WO | 2013169751 A1 | 11/2013 |
| WO | 2012058463 A3 | 4/2014 |
| WO | 2014144129 A2 | 9/2014 |
| WO | 2014144129 A3 | 2/2015 |
| WO | 2016024627 A1 | 2/2016 |
| WO | 2017118639 A1 | 7/2017 |
| WO | 2017181367 A1 | 10/2017 |
| WO | 2018027013 A1 | 2/2018 |
| WO | WO-2019084033 A1 * | 5/2019 ............. A61P 15/00 |
| WO | 2020061590 A1 | 3/2020 |
| WO | 2020206462 A1 | 10/2020 |
| WO | 2020247756 A1 | 12/2020 |
| WO | 2021061847 A1 | 4/2021 |
| WO | 2022099319 A1 | 5/2022 |
| WO | 2022211810 A1 | 10/2022 |

OTHER PUBLICATIONS

Vaiman et al., "Genetic Regulation of Recurrent Spontaneous Abortion in Humans", Biomedical Journal, vol. 38, No. 1, Jan.-Feb. 2015, pp. 11-24, doi: 10.4103/2319-4170.133777.

Vedernikov et al., "The Role of Cyclic Nucleotides in the Spontaneous Contractility and Responsiveness to Nitric Oxide of the Rat Uterus at Midgestation and Term", American Journal of Obstetrics & Gynecology, vol. 182, No. 3, Mar. 1, 2000, pp. 612-619, XP029483652, ISSN: 0002-9378, doi: 10.1067/mob.2000.104203.

Verhaar et al., "A single chain Fv derived from a filamentous phage library has distinct tumour targeting advantages over one derived from a hybridoma", International Journal of Cancer, vol. 61, No. 4, May 16, 1995, pp. 497-501, doi: 10.1002/ijc.2910610412.

Vuckovic et al., "Current trends and challenges in sample preparation for global metabolomics using liquid chromatography-mass spectrometry", Analytical and Bioanalytical Chemistry, vol. 403, No. 6, May 12, 2012, pp. 1523-1548, doi: 10.1007/s00216-012-6039-y.

Walejko et al., "Chronic maternal cortisol excess during late gestation leads to metabolic alterations in the newborn heart", American Journal of Physiology: Endocrinology and Metabolism, vol. 316, No. 3, Jan. 8, 2019, pp. E546-E556, doi: 10.1152/ajpendo.00386.2018.

Walejko et al., "Multiomics approach reveals metabolic changes in the heart at birth", American Journal of Physiology: Endocrinology and Metabolism, vol. 315, No. 6, Oct. 9, 2018, pp. E1212-E1223, doi: 10.1152/ajpendo.00297.2018.

Wang et al., "Metabolic profiling of pregnancy: cross-sectional and longitudinal evidence", BMC Medicine, vol. 14, No. 205, Dec. 13, 2016, 14 pgs., doi: 10.1186/s12916-016-0733-0.

Want et al., "Challenges in applying chemometrics to LC-MS-based global metabolite profile data", Bioanalysis, vol. 1, No. 4, Jul. 2009, pp. 805-819, doi: 10.4155/bio.09.64.

Wierrani et al., "Elevated serum melatonin levels during human late pregnancy and labour", Journal of the Institute of Obstetrics & Gynaecology, vol. 17, No. 5, Sep. 1997, pp. 449-451, doi: 10.1080/01443619750112411.

Willatts et al., "Effect of long-chain polyunsaturated fatty acids in infant formula on problem solving at 10 months of age", Lancet, vol. 352, No. 9129, Aug. 29, 1998, pp. 688-691, doi: 10.1016/s0140-6736(97)11374-5.

Winter et al., "Man-made antibodies", Nature, vol. 349, Jan. 24, 1991, pp. 293-299.

Xia et al., "MetPA: a web-based metabolomics tool for pathway analysis and visualization", Bioinformatics, vol. 26, No. 18, Sep. 15, 2010, pp. 2342-2344, first published Jul. 13, 2010, doi: 10.1093/bioinformatics/btq418.

Xia et al., "MSEA: a web-based tool to identify biologically meaningful patterns in quantitative metabolomic data", Nucleic Acids Research, vol. 38 (Web Server issue), Jul. 2010, pp. W71-W77, published online May 10, 2010, doi: 10.1093/nar/gkq329.

Yamauchi et al., "Machine Learning Approaches to Predict Gestational age in Normal and Complicated Pregnancies via Urinary Metabolomics Analysis", Scientific Reports, vol. 11, No. 1, Sep. 7, 2021, XP093189830, ISSN: 2045-2322, doi: 10.1038/s41598-021-97342-z.

Yan et al., "BCFA-enriched vernix-monoacylglycerol reduces LPS-induced inflammatory markers in human enterocytes in vitro", Pediatric Research, vol. 83, No. 4, Apr. 2018, pp. 874-879, doi: 10.1038/pr.2017.297.

Zhang et al., "A general framework for weighted gene co-expression network analysis", Statistical Applications in Genetics and Molecular Biology, vol. 4, Article 17, Aug. 12, 2005, 11 pgs., doi: 10.2202/1544-6115.1128.

Zheng et al., "Metabolic Signature of Pregnant Women with Neural Tube Defects in Offspring", Journal of Proteome Research, vol. 10, No. 10, Sep. 8, 2011, pp. 4845-4854, doi: 10.1021/pr200666d.

Zizzo et al., "Can Guanine-Based Purines be Considered Modulators of Intestinal Motility In Rodents?", European Journal of Phar-

(56) References Cited

OTHER PUBLICATIONS macology, Elsevier Science, NL, vol. 650, No. 1, Jan. 10, 2011, pp. 350-355, XP027538860, ISSN: 0014-2999, doi: 10.1016/j.ejphar.2010.09.062.
Zou et al., "Regularization and Variable Selection via the Elastic Net", Journal of the Royal Statistical Society. Series B (Statistical Methodology), vol. 67, No. 2, Mar. 9, 2005, pp. 301-320, doi: 10.1111/j.1467-9868.2005.00503.x.
Dawson et al., "Sulphate in Pregnancy", Nutrients, vol. 7, No. 3, Mar. 4, 2015, pp. 1594-1606, doi: 10.3390/nu7031594.
Delnord et al., "Varying Gestational Age Patterns in Cesarean Delivery: An International Comparison", BMC Pregnancy and Childbirth, Biomed Central Ltd, London, GB, vol. 14, No. 1, Sep. 13, 2014, p. 321, XP021196868, doi: 10.1186/1471-2393-14-321.
Dudzik et al., "Metabolic fingerprint of Gestational Diabetes Mellitus", Journal of Proteomics, vol. 103, May 30, 2014, pp. 57-71, published online Mar. 31, 2014, doi: 10.1016/j.jprot.2014.03.025.
Eckhart et al., "Metabolomics as a Key Integrator for "Omic" Advancement of Personalized Medicine and Future Therapies", Clinical and Translational Science, vol. 5, No. 3, Jun. 11, 2012, pp. 285-288.
Feunang et al., "ClassyFire: automated chemical classification with a comprehensive, computable taxonomy", Journal of cheminformatics, vol. 8, No. 61, Nov. 4, 2016, 20 pgs., doi: 10.1186/s13321-016-0174-y.
Friedman, "Greedy Function Approximation: A Gradient Boosting Machine", The Annals of Statistics, vol. 29, No. 5, Oct. 2001, pp. 1189-1232.
Gagnon et al., "Obstetrical complications associated with abnormal maternal serum markers analytes", Journal of Obstetrics Gynaecology Canada, vol. 30, No. 10, Oct. 2008, pp. 918-932, doi: 10.1016/S1701-2163(16)32973-5.
GBD 2013 Mortality & Causes of, Death Collaborators "Global, regional, and national age—sex specific all-cause and cause-specific mortality for 240 causes of death, 1990-2013: a systematic analysis for the Global Burden of Disease Study 2013", Lancet, vol. 385, No. 9963, Jan. 10, 2015, pp. 117-171, doi: 10.1016/S0140-6736(14)61682-2.
Goeman et al., "A global test for groups of genes: testing association with a clinical outcome", Bioinformatics, vol. 20, No. 1, Jan. 1, 2004, pp. 93-99, doi: 10.1093/bioinformatics/btg382.
Goeman et al., "Analyzing gene expression data in terms of gene sets: methodological issues", Bioinformatics, vol. 23, No. 8, Apr. 15, 2007, pp. 980-987, published online Feb. 15, 2007, doi: 10.1093/bioinformatics/btm051.
Guijas et al., "Metlin: A Technology Platform for Identifying Knowns and Unknowns", Analytical Chemistry, vol. 90, No. 5, Mar. 6, 2018, pp. 3156-3164, published online Feb. 8, 2018, doi: 10.1021/acs.analchem.7b04424.
Harlow et al., "Antibodies: A Laboratory Manual", Cold Spring Harbor Laboratory, 1988, 2 pgs.
Hastie et al., "Principal Curves", Journal of the American Statistical Association, vol. 84, No. 406, Jun. 1989, pp. 502-516, doi: 10.1080/01621459.1989.10478797.
Hill et al., "Dehydroepiandrosterone, Its Metabolites and Ion Channels", Journal of Steroid Biochemistry & Molecular Biology, Elsevier Science Ltd., Oxford, GB, vol. 145, May 17, 2014, pp. 293-314, XP029112249, ISSN: 0960-0760, doi: 10.1016/J.JSBMB.2014.05.006.
Hogberg et al., "Maternal Mortality in Sweden, 1980-1988", Obstetrics and Gynecology, vol. 84, No. 2, Aug. 1994, pp. 240-244, doi: 10.1097/00132586-199504000-00027.
Hunter et al., "Preparation of iodine-131 labelled human growth hormone of high specific activity", Nature, vol. 194, 1962, pp. 495-496.
Hyotylainen, "Novel methodologies in metabolic profiling with a focus on molecular diagnostic applications", Expert Review of Molecular Diagnostics, vol. 12, No. 5, Jun. 2012, pp. 527-538, doi: 10.1586/erm.12.33.

Jacob et al., "Maternal Mortality in Utah", Obstetrics and Gynecology, vol. 91, No. 2, Feb. 1998, pp. 187-191, doi: 10.1016/s0029-7844(97)00664-9.
Johnson et al., "Metabolomics: beyond biomarkers and towards mechanisms", Nature Reviews Molecular Cell Biology, vol. 17, No. 7, Jul. 2016, pp. 451-459, published online Mar. 16, 2016, doi: 10.1038/nrm.2016.25.
Jungblut et al., "Protein identification from 2-DE gels by MALDI mass spectrometry", Mass Spectrometry Reviews, vol. 16, No. 3, 1997, pp. 145-162, doi: 10.1002/(SICI)1098-2787(1997)16:3<145::AID-MAS2>3.0.CO;2-H.
Kaddurah-Daouk, "Metabolomics: a global biochemical approach to drug response and disease", Annual Review of Pharmacology and Toxicology, vol. 48, 2008, pp. 653-683, doi: 10.1146/annurev.pharmtox.48.113006.094715.
Kanehisa et al., "KEGG: kyoto encyclopedia of genes and genomes", Nucleic Acids Research, vol. 28, No. 1, Jan. 1, 2000, pp. 27-30, doi: 10.1093/nar/28.1.27.
Kang et al., "Antibody redesign by chain shuffling from random combinatorial immunoglobulin libraries", Proceedings of the National Academy of Sciences of the United States of America, vol. 88, No. 24, Dec. 15, 1991, pp. 11120-11123, doi: 10.1073/pnas.88.24.11120.
Kenny et al., "Robust Early Pregnancy Prediction of Later Preeclampsia Using Metabolomic Biomarkers", Hypertension, vol. 56, No. 4, Oct. 1, 2010, pp. 741-749, doi: 10.1161/HYPERTENSIONAHA.110.157297.
Kilpatrick et al., "Preventability of maternal deaths: comparison between Zambian and American referral hospitals", Obstetrics and Gynecology, vol. 100, No. 2, Aug. 2002, pp. 321-326, doi: 10.1016/s0029-7844(02)02065-3.
Kind et al., "LipidBlast in silico tandem mass spectrometry database for lipid identification", Nature Methods, vol. 10, No. 8, Aug. 2013, pp. 755-758, first published Jun. 30, 2013, doi: 10.1038/nmeth.2551.
Kingsmore, "Multiplexed protein measurement: technologies and applications of protein and antibody arrays", Nature Reviews Drug Discovery, vol. 5, No. 4, Apr. 2006, pp. 310-321, doi: 10.1038/nrd2006.
Klebanoff et al., "Serum caffeine and paraxanthine as markers for reported caffeine intake in pregnancy", Annals of epidemiology, vol. 8, No. 2, Feb. 1998, pp. 107-111, doi: 10.1016/s1047-2797(97)00125-7.
Knottnerus et al., "Disorders of mitochondrial long-chain fatty acid oxidation and the carnitine shuttle", Reviews in Endocrine and Metabolic Disorders, vol. 19, No. 1, Mar. 2018, pp. 93-106, doi: 10.1007/s11154-018-9448-1.
Knutti et al., "Effect of pregnancy on the pharmacokinetics of caffeine", European Journal of Clinical Pharmacology, vol. 21, No. 2, 1981, pp. 121-126, doi: 10.1007/BF00637512.
Kohler et al., "Continuous cultures of fused cells secreting antibody of predefined specificity", Nature, vol. 256, Aug. 7, 1975, pp. 495-497, doi: 10.1038/256495a0.
Kozbor et al., "Specific immunoglobulin production and enhanced tumorigenicity following ascites growth of human hybridomas", Journal of Immunological Methods, vol. 81, No. 1, Jul. 16, 1985, pp. 31-42, doi: 10.1016/0022-1759(85)90119-x.
Kraly et al., "Review: Microfluidic applications in metabolomics and metabolic profiling", Analytica Chimica Acta, vol. 653, No. 1, Oct. 19, 2009, pp. 23-35, doi: 10.1016/j.aca.2009.08.037.
Kubli-Garfias et al., "In Vitro Effects of Androgens Upon the Spontaneous Rat Uterine Contractility", Steroids, vol. 35, No. 6, Jun. 30, 1980, pp. 633-641, doi: 10.1016/0039-128x(80)90088-4.
Liang et al., "Metabolic Dynamics and Prediction of Gestational Age and Time to Delivery in Pregnant Women", Cell, Amsterdam NL, vol. 181, No. 7, Jun. 25, 2020, pp. 1680-1692.e15, XP086202863, ISSN: 0092-8674, doi: 10.1016/j.cell.2020.05.002.
Lockwood et al., "Preterm labor: Clinical findings, diagnostic evaluation, and initial treatment", UpToDate, retrieved from https://www.uptodate.com/contents/preterm-labor-clinical-findings-diagnostic-evaluation-and-initial-treatment, retrieved on Sep. 2019, 22 pgs.
Lopez-Hernandez et al., "Urinary Metabolites Altered during the Third Trimester in Pregnancies Complicated by Gestational Diabe-

(56) References Cited

OTHER PUBLICATIONS tes Mellitus: Relationship with Potential Upcoming Metabolic Disorders", Internal Journal of Molecular Sciences, vol. 20, No. 1186, Mar. 8, 2019, 16 pgs., doi: 10.3390/ijms20051186.

Luke et al., "The evidence linking maternal nutrition and prematurity", Journal of Perinatal Medicine, vol. 33, No. 6, Dec. 1, 2005, pp. 500-505, doi: 10.1515/JPM.2005.088.

Maere et al., "BiNGO: a Cytoscape plugin to assess overrepresentation of Gene Ontology categories in Biological Networks", Bioinformatics, vol. 21, No. 16, Aug. 15, 2005, pp. 3448-3449, doi: 10.1093/bioinformatics/bti551.

Maitre et al., "Urinary Metabolic Profiles in Early Pregnancy are Associated with Preterm Birth and Fetal Growth Restriction in the Rhea Mother-Child Cohort Study", BMC Medicine, Biomed Central Ltd., London, GB, vol. 12, No. 110, Jul. 11, 2014, 14 pgs., XP021190817, ISSN: 1741-7015, doi: 10.1186/1741-7015-12-110.

Majewska et al., "Modulation of Uterine GABAA Receptors During Gestation and by Tetrahydroprogesterone", European Journal of Pharmacology, Elsevier Science, NL, vol. 174, No. 1, Dec. 12, 1989, pp. 43-47, XP023770278, ISSN: 0014-2999, doi: 10.1016/0014-2999(89)90871-6.

Mallender et al., "Construction, Expression, and Activity of a Bivalent Bispecific Single-chain Antibody", The Journal of Biological Chemistry, Jan. 7, 1994, vol. 269, No. 1, pp. 199-206, doi: 10.1016/S0021-9258(17)42334-9.

Maltepe et al., "Placenta: the forgotten organ", Annual Review of Cell and Developmental Biology, 2015, vol. 31, pp. 523-552, published online Oct. 5, 2015, doi: 10.1146/annurev-cellbio-100814-125620.

Martin et al., "Births: Final Data for 2017", National Vital Statistics Report, Nov. 7, 2018, vol. 67, No. 8, pp. 1-50.

Maslova et al., "Prenatal n-3 long-chain fatty acid status and offspring metabolic health in early and mid-childhood: results from Project Viva", Nutrition & Diabetes, May 25, 2018, vol. 8, No. 29, 16 pgs., doi: 10.1038/s41387-018-0040-2.

Maubert et al., "A Liquid Chromatography/Tandem Mass Spectometry Profile of 16 Serum Steroids, Including 21-Deoxycortisol and 21-Deoxycorticosterone, for Management of Congenital Adrenal Hyperplasia", Journal of the Endocrine Society, vol. 1, No. 3, Feb. 10, 2017, pp. 186-201, doi: 10.1210/js.2016-1048.

Mendelson, "Minireview: fetal-maternal hormonal signaling in pregnancy and labor", Molecular endocrinology, vol. 23, No. 7, Jul. 2009, pp. 947-954, published online Mar. 12, 2009, doi: 10.1210/me.2009-0016.

Mertz et al., "Pregnancy-Related Mortality in New Jersey, 1975 to 1989", American Journal of Public Health, vol. 82, No. 8, Aug. 1992, pp. 1085-1088, doi: 10.2105/ajph.82.8.1085.

Milczarek et al., "Melatonin enhances antioxidant action of alpha-tocopherol and ascorbate against NADPH- and iron-dependent lipid peroxidation in human placental mitochondria", Journal of Pineal Research, Sep. 2010, vol. 49, No. 2, pp. 149-155, published online May 26, 2010, doi: 10.1111/j.1600-079X.2010.00779.x.

Miliku et al., "Maternal vitamin D concentrations during pregnancy, fetal growth patterns, and risks of adverse birth outcomes", American Society for Nutrition, Printed in USA, vol. 103, No. 6, Jun. 2016, pp. 1514-1522, doi: 10.3945/ajcn.115.123752.

Mitznegg et al., "The Influence of Caffeine on Endogenous Cyclic 3', 5'-AMP and Uterine Smooth Muscle Contraction Induced by Oxytocin", Life Science, Pergamon Press, Oxford, GB, vol. 9, No. 17, Sep. 1, 1970, pp. 975-981, XP023723820, ISSN: 0024-3205, doi: 10.1016/0024-3205(70)90120-7.

Monteiro et al., "Metabolomics analysis for biomarker discovery: advances and challenges", Current Medicinal Chemistry, vol. 20, No. 2, 2013, pp. 257-271, doi: 10.2174/092986713804806621.

Morrison et al., "Chimeric human antibody molecules: Mouse antigen-binding domains with human constant region domains", Proceedings of the National Academy of Sciences of the United States of America, vol. 81, No. 21, Nov. 1984, pp. 6851-6855, doi: 10.1073/pnas.81.21.6851.

Nakamura et al., "Changes of serum melatonin level and its relationship to feto-placental unit during pregnancy", Journal Pineal Research, vol. 30, No. 1, Jan. 2001, pp. 29-33, doi: 10.1034/j.1600-079x.2001.300104.x.

Neuberger et al., "Recombinant antibodies possessing novel effector functions", Nature, vol. 312, Dec. 13, 1984, pp. 604-608, doi: 10.1038/312604a0.

Ngo et al., "Noninvasive Blood Tests for Fetal Development Predict Gestational Age and Preterm Delivery", Science, Jun. 8, 2018, vol. 360, No. 6393, pp. 1133-1136, doi: 10.1126/science.aar3819.

Nicholls et al., "An improved method for generating single-chain antibodies from hybridomas", Journal of Immunological Methods, vol. 165, No. 1, Sep. 27, 1993, pp. 81-91, doi: 10.1016/0022-1759(93)90109-k.

Norwitz et al., "Progesterone supplementation to reduce the risk of spontaneous preterm birth", UpToDate, retrieved from https://www.uptodate.com/contents/progesterone-supplementation-to-reduce-the-risk-of-spontaneous-preterm-birth, retrieved on Sep. 6, 2019, 25 pgs.

Nygren, "Conjugation of horseradish peroxidase to Fab fragments with different homobifunctional and heterobifunctional cross-linking reagents. A comparative study.", Journal of Histochemistry and Cytochemistry, vol. 30, No. 5, May 1982, pp. 407-412.

O'Connell, "Recent advances in metabolomics in oncology", Bioanalysis, vol. 4, No. 4, Mar. 7, 2012, pp. 431-451, doi: 10.4155/bio.11.326.

Orlandi et al., "Cloning immunoglobulin variable domains for expression by the polymerase chain reaction", Proceedings of the National Academy of Sciences of the United States of America, vol. 86, No. 10, May 1989, pp. 3833-3837, doi: 10.1073/pnas.86.10.3833.

Pain et al., "Preparation of protein A-peroxidase monoconjugate using a heterobifunctional reagent, and its use in enzyme immunoassays", Journal of Immunological Methods, vol. 40, No. 2, Jan. 30, 1981, pp. 219-230, doi: 10.1016/0022-1759(81)90068-5.

Panezai et al., "Correlation of serum cytokines, chemokines, growth factors and enzymes with periodontal disease parameters", PLoS One, vol. 12, No. 11, Nov. 30, 2017, pp. 1-17, doi: 10.1371/journal.pone.0188945.

Paoletti et al., "Observational study on the stability of the psychological status during normal pregnancy and increased blood levels of neuroactive steroids with GABA-A receptor agonist activity", Psychoneuroendocrinology, vol. 31, No. 4, May 2006, pp. 485-492, doi: 10.1016/j.psyneuen.2005.11.006.

Papageorghiou et al., "Ultrasound-based gestational-age estimation in late pregnancy", Ultrasound in Obstetrics & Gynecology, vol. 48. No. 6, Dec. 2016, pp. 719-726, doi: 10.1002/uog.15894.

Park et al., "Plasma Levels of Lysine, Tyrosine, and Valine During Pregnancy Are Independent Risk Factors of Insulin Resistance and Gestational Diabetes", Metabolic Syndrome and Related Disorders, vol. 13, No. 2, Mar. 2015, pp. 64-70, doi: 10.1089/met.2014.0113.

Perusquia et al., "Androgens Induce Relaxation of Contractile Activity in Pregnant Human Myometrium at Term: A Nongenomic Action on L-Type Calcium Channels[1]", Biology of Reproduction, Mar. 9, 2005, vol. 73, No. 2, pp. 214-221, doi: 10.1095/biolreprod.104.036954.

Perusquia et al., "Non-Genomic Mechanism of Action Of Δ-4 And 5-Reduced Androgens and Progestins on the Contractility of the Isolated Rat Myometrium", Life Science, vol. 47, No. 17, Jan. 1, 1990, pp. 1547-1553, XP025566940, ISSN: 0024-3205, doi: 10.1016/0024-3205(90)90183-r.

Prentice et al., "Energy adaptations in human pregnancy: limits and long-term consequences", The American Journal of Clinical Nutrition, vol. 71, No. 5, May 1, 2000, pp. 1226S-1232S, doi: 10.1093/ajcn/71.5.1226s.

Robinson et al., "Pregnancy loss", Best Practice and Research Clinical Obstetrics and Gynecology, vol. 28, No. 1, Jan. 2014, pp. 169-178, doi: 10.1016/j.bpobgyn.2013.08.012.

Romero et al., "Metabolomics in premature labor: a novel approach to identify patients at risk for preterm delivery", Journal of Maternal-Fetal Neonatal Medicine, vol. 23, No. 12, Dec. 2010, pp. 1344-1359, published online May 26, 2010, doi: 10.3109/14767058.2010.482618.

(56) References Cited

OTHER PUBLICATIONS

Romero et al., "The Maternal Plasma Proteome Changes as a Function of Gestational Age in Normal Pregnancy: a Longitudinal Study", American Journal of Obstetrics and Gynecology, vol. 217, No. 1, Jul. 2017, pp. 67.e1-67.e21, doi: 10.1016/j.ajog.2017.02.037.
Rosenthal et al., "Nanobiotechnology Protocols", Methods in Molecular Biology, 2005, vol. 303, 241 pgs.
Rubens et al., "Global report on preterm birth and stillbirth (7 of 7): mobilizing resources to accelerate innovative solutions (Global Action Agenda)", BMC Pregnancy Childbirth, vol. 10, No. (Suppl 1): S7, Feb. 23, 2010, 17 pgs., doi: 10.1186/1471-2393-10-S1-S7.
Rusling et al., "Measurement of biomarker proteins for point-of-care early detection and monitoring of cancer", Analyst, vol. 135, No. 10, Jul. 8, 2010, pp. 2496-2511, doi: 10.1039/c0an00204f.
Ryckman et al., "Association of amino acids with common complications of prematurity", Pediatric Research, vol. 73, No. 6, Jun. 2013, pp. 700-705, doi: 10.1038/pr.2013.43.
Ryckman et al., "Maternal factors and complications of preterm birth associated with neonatal thyroid stimulating hormone", Journal of Pediatric Endocrinology & Metabolism, vol. 27, No. 9-10, Sep. 2014, pp. 929-938, doi: 10.1515/jpem-2013-0366.
Ryckman et al., "Pregnancy-Related Changes of Amino Acid and Acylcarnitine Concentrations: The Impact of Obesity", AJP Reports, vol. 6, No. 3, Jul. 2016, pp. e329-e336, doi: 10.1055/s-0036-1592414.
Sabhachandani et al., "Microsphere-based immunoassay integrated with a microfluidic network to perform logic operations", Microchim Acta, May 14, 2015, vol. 182, pp. 1835-1840, doi: 10.1007/s00604-015-1518-4.
Sachse et al., "Metabolic changes in urine during and after pregnancy in a large, multiethnic population-based cohort study of gestational diabetes", PLoS One, 2012, vol. 7, No. 12, e52399, 12 pgs., published online Dec. 21, 2012, doi: 10.1371/journal.pone.0052399.
Say et al., "Global causes of maternal death: a WHO systematic analysis", Lancet Global Health, vol. 2, No. 6, Jun. 2014, pp. e323-e333, published online May 5, 2014, doi: 10.1016/S2214-109X(14)70227-X.
Scommegna et al., "The Effect of Pregnenolone Sulfate on Uterine Contractility", American Journal of Obstetrics and Gynecology, vol. 108, No. 7, Dec. 1, 1970, pp. 1023-1029, XP009540350, doi: 10.1016/0002-9378(70)90447-3.
Sepulveda et al., "Congenital diaphragmatic hernia in a first-trimester ultrasound aneuploidy screening program", Prenatal Diagnosis, vol. 28, No. 6, Jun. 2008, pp. 531-554, doi: 10.1002/pd.2019.
Sevastou et al., "Lysoglycerophospholipids in chronic inflammatory disorders: the PLA(2)/LPC and ATX/LPA axes", Biochimica et Biophysica Acta (BBA)—Molecular and Cell Biology of Lipids, vol. 1831, No. 1, Jan. 2013, pp. 42-60, published online Jul. 31, 2012, doi: 10.1016/j.bbalip.2012.07.019.
Sim et al., "Rat Uterine Contractility and the Activities of Uterine Adenyl Cyclase and Phosphodiesterase During the Estrus Cycle", Biochemical Pharmacology, Elsevier, Us, vol. 22, No. 12, Jun. 15, 1973, pp. 1417-1422, XP023757210, ISSN: 0006-2952, doi: 10.1016/0006-2952(73)90319-5.
Simhan et al., "Inhibition of acute preterm labor", UpToDate, retrieved from https://www.uptodate.com/contents/inhibition-of-acute-preterm-labor, retrieved on Sep. 16, 2019, 29 pgs.
Simmons et al., "Prophylactic and Therapeutic Efficacy of Human Monoclonal Antibodies against H5N1 Influenza", PLoS Medicine, vol. 4, No. 5, e178, May 29, 2007, pp. 0928-0936, doi: 10.1371/journal.pmed.0040178.
Sreekumara et al., "Metabolomic profiles delineate potential role for sarcosine in prostate cancer progression", Nature, vol. 457, No. 7231, Feb. 12, 2009, pp. 910-914, doi: 10.1038/nature07762.
Takeda et al., "Construction of chimaeric processed immunoglobulin genes containing mouse variable and human constant region sequences", Nature, vol. 314, No. 6010, Apr. 4, 1985, pp. 452-454, doi: 10.1038/314452a0.
Tamura et al., "Melatonin and female reproduction", Journal of Obstetrics and Gynaecology Research, vol. 40, No. 1, Jan. 2014, pp. 1-11, published online Oct. 7, 2013, doi: 10.1111/jog.12177.
Tan et al., "Tocolytic treatment for the management of preterm labour: A systematic review", Singapore Medical Journal, vol. 47, No. 5, Jun. 2006, pp. 361-366.
Tibshirani, "Regression Shrinkage and Selection via the Lasso", Journal of the Royal Statistical Society, series. B, vol. 58, No. 1, 1996, pp. 267-288.
Trivedi et al., "HILIC-MS-Based Shotgun Metabolomic Profiling of Maternal Urine at 9-23 Weeks of Gestation—Establishing the Baseline Changes in the Maternal Metabolome", Biomedical Chromatography, John Wiley & Sons Ltd, GB, vol. 29, No. 2, Jun. 5, 2014, pp. 240-245, XP071549259, ISSN: 0269-3879, doi: 10.1002/bmc.3266.
Tulandi et al., "Management of couples with recurrent pregnancy loss", UpToDate, retrieved from https://www.uptodate.com/contents/recurrent-pregnancy-loss-management, retrieved on Sep. 6, 2019, 17 pgs.
Tusher et al., "Significance analysis of microarrays applied to the ionizing radiation response", Proceedings of the National Academy of Sciences of the United States of America, vol. 98, No. 9, Apr. 24, 2001, pp. 5116-5121, doi: 10.1073/pnas.091062498.
Extended European Search Report for European Application No. 19862408.2, Search completed Apr. 22, 2022, Mailed May 3, 2022, 15 pgs.
Extended European Search Report for European Application No. 21890353.2, Search completed Jul. 29, 2024, Mailed Aug. 6, 2024, 11 pgs.
Extended European Search Report for European Application No. 21935395.0, Search completed Jan. 22, 2025, Mailed Jan. 30, 2025, 23 pgs.
Extended European Search Report for European Application No. 20869395.2, Search completed Sep. 22, 2023, Mailed Oct. 4, 2023, 8 pgs.
International Preliminary Report on Patentability for International Application PCT/US2019/052515, Report issued Mar. 23, 2021, Mailed Apr. 1, 2021, 11 pgs.
International Preliminary Report on Patentability for International Application No. PCT/US2021/025268, Report issued Oct. 3, 2023, Mailed Oct. 12, 2023, 11 pgs.
International Preliminary Report on Patentability for International Application PCT/US2020/052311, Report issued Mar. 15, 2022, Mailed on Apr. 7, 2022, 7 pgs.
International Preliminary Report on Patentability for International Application PCT/US2021/072295, Report issued May 8, 2023, Mailed on May 19, 2023, 07 pgs.
International Search Report and Written Opinion for International Application No. PCT/US2020/052311, Search completed Feb. 10, 2021, Mailed Mar. 3, 2021, 14 pgs.
International Search Report and Written Opinion for International Application No. PCT/US2019/052515, Search completed Nov. 11, 2019, Mailed Dec. 5, 2019, 21 pgs.
International Search Report and Written Opinion for International Application No. PCT/US2021/025268, Search completed Aug. 11, 2021, Mailed Sep. 14, 2021, 19 pgs.
International Search Report and Written Opinion for International Application No. PCT/US2021/072295, Search completed Jan. 7, 2022, Mailed Feb. 3, 2022, 17 pgs.
Supplementary Partial European Search Report for European Application No. 21935395.0, Search completed Oct. 15, 2024, Mailed Oct. 21, 2024, 18 pgs.
"About Preterm Labor and Birth", National Institutes of Health, Nov. 2014, 3 pgs.
"Maternal and Infant Health", Centers for Disease Control and Prevention, 3 pgs., https://www.cdc.gov/reproductivehealth/maternalinfanthealth/pretermbirth.html.
"Modulation of Ghrelin Secretion, Novel Therapeutic Target for Obesity", Retrieved from the Internet: URL:http://www.liv.ac.uk/physiology/eventsandnews/news/september07.doc.Internet Citation, Sep. 1, 2007, 11 pgs., XP002513113.

(56) References Cited

OTHER PUBLICATIONS

"Preterm birth", World Health Organization, Retrieved from the internet: http://www.who.int/mediacentre/factsheets/fs363/en/, Nov. 2014, 4 pgs.

"What are the risk factors for preterm labor and birth?", National Institutes of Health, Retrieved from the internet: https://www.nichd.nih.gov/health/topics/preterm/conditioninfo/Pages/who_risk.aspx, Nov. 2014, 3 pgs.

Afors et al., "Use of Continuous Electronic Fetal Monitoring in a Preterm Fetus: Clinical Dilemmas and Recommendations for Practice", Journal of Pregnancy, Jan. 1, 2011, vol. 2011, pp. 1-7, XP055693733, doi: 10.1155/2011/848794.

Aghaeepour et al., "An immune clock of human pregnancy", Science Immunology, Sep. 1, 2017, vol. 2, eaan2946, 11 pgs.

Alkema et al., "Global, regional, and national levels and trends in maternal mortality between 1990 and 2015, with scenario-based projections to 2030: A systematic analysis by the UN Maternal Mortality Estimation Inter-Agency Group", Lancet, vol. 387, No. 10017, Jan. 30, 2016, pp. 462-474, published online Nov. 13, 2015, doi: 10.1016/S0140-6736(15)00838-7.

Andreolini et al., "Improved determination of estriol-16α-glucuronide in pregnancy urine by direct liquid chromatography with fluorescence detection", Clinical Chemistry, vol. 31, No. 1, 1985, pp. 124-126.

Bahado-Singh et al., "Metabolomics and first-trimester prediction of early-onset preeclampsia", The Journal of Maternal-Fetal and Neonatal Medicine, vol. 25, No. 10, Oct. 2012, pp. 1840-1847, doi: 10.3109/14767058.2012.680254.

Beckonert et al., "Metabolic profiling, metabolomic and metabonomic procedures for NMR spectroscopy of urine, plasma, serum and tissue extracts", Nature Protocols, vol. 2, No. 11, 2007, pp. 2692-2703, published online Oct. 25, 2007, doi: 10.1038/nprot.200.376.

Berg et al., "Preventability of pregnancy-related deaths: results of a state-wide review", Obstetrics and Gynecology, vol. 106, No. 6, Dec. 2005, pp. 1228-1234, doi: 10.1097/01.AOG.0000187894.71913.e8.

Berge et al., "Pharmaceutical Salts", Journal of Pharmaceutical Sciences, vol. 66, No. 1, Jan. 1977, pp. 1-19.

Biro et al., "Urinary Steroid Profile in Early Pregnancy after in Vitro Fertilization", Acta Obstetricia Gynecologica Scandinavica, vol. 91, No. 5, May 2012, pp. 625-629, doi: 10.1111/j.1600-0412.2012.01387.x.

Bispham et al., "Maternal endocrine adaptation throughout pregnancy to nutritional manipulation: consequences for maternal plasma leptin and cortisol and the programming of fetal adipose tissue development", Endocrinology, vol. 144, No. 8, Aug. 2003, pp. 3575-3585. doi: 10.1210/en.2003-0320.

Blencowe et al., "National, regional, and worldwide estimates of stillbirth rates in 2015, with trends from 2000: a systematic analysis", Lancet Global Health, vol. 4, No. 2, Feb. 2016, pp. e98-e108, doi: 10.1016/S2214-109X(15)00275-2.

Bonacossa et al., "Effect of Corticosterone, Hydrocortisone and Prostaglandin Fatty Acid Precursors on the Spontaneous Motility of the Uterus Isolated from Ovariectomized Rats", Prostaglandins, vol. 23, No. 1, Jan. 31, 1982, pp. 113-128, doi: 10.1016/0090-6980(82)90027-2.

Bouvier-Colle et al., "Maternal deaths and substandard care: the results of a confidential survey in France", European Journal of Obstetrics and Gynecology and Reproductive Biology, vol. 58, No. 1, Jun. 1995, pp. 3-7, doi: 10.1016/0028-2243(94)01976-e.

Brown et al., "Plasma Concentrations of Carbohydrates and Sugar Alcohols in Term Newborns after Milk Feeding", Pediatric research, vol. 64, No. 2, Aug. 2008, pp. 189-193, doi: 10.1203/PDR.0b013e3181761888, PMID: 18391836, PMCID: PMC2903005.

Bruyn et al., "Carnitine Deficiency and Pregnancy", Case Reports in Obstetrics and Gynecology, vol. 2015, No. 101468, 2015, 4 pgs., doi: 10.1155/2015/101468.

Burns, "Inhibition of Rat Uterine Contractility by Dehydroepiandrosterone Sulphate", Journal of Physiology, Database Embase [Online], Elsevier Science Publishers, Amsterdam, NL; Database accession No. EMB-10109710, 1980 GB, vol. 300, pp. 54P, ISSN: 0022-3751, XP002812339.

Cao et al., "Association study between methylenetetrahydrofolate reductase polymorphisms and unexplained recurrent pregnancy loss: a meta-analysis", Gene, vol. 514, No. 2, Feb. 10, 2013, pp. 105-111, doi: 10.1016/j.gene.2012.10.091.

Chan et al., "Cord blood thyroid-stimulating hormone level in high-risk pregnancies", European Journal of Obstetrics & Gynecology and Reproductive Biology, vol. 108, No. 2, Jun. 10, 2003, pp. 142-145, doi: 10.1016/S0301-2115(02)00418-9.

Chan et al., "Cord blood thyroid-stimulating hormone level in twin pregnancy", Acta Obstetricia et Gynecologica Scandinavica, vol. 82, No. 1, Jan. 2003, pp. 28-31, doi: 10.1034/j.1600-0412.2003.820105.x.

Chong et al., "MetaboAnalyst 4.0: towards more transparent and integrative metabolomics analysis", Nucleic Acids Research, vol. 46, No. W1, Jul. 2, 2018, pp. W486-W494, published online May 14, 2018, doi: 10.1093/nar/gky310.

Clark et al., "Maternal death in the 21st century: causes, prevention, and relationship to cesarean delivery", American Journal of Obstetrics and Gynecology, Jul. 2008, vol. 199, No. 1, pp. 36.e1-36.e5, doi: 10.1016/j.ajog.2008.03.007.

Cole et al., "Human monoclonal antibodies", Molecular and Cellular Biochemistry, vol. 62, Sep. 1984, pp. 109-120.

Coloma et al., "Design and production of novel tetravalent bispecific antibodies", Nature Biotechnology, vol. 15, Feb. 1, 1997, pp. 159-163, doi: 10.1038/nbt0297-159.

Conde-Agudelo et al., "Maternal-perinatal morbidity and mortality associated with adolescent pregnancy in Latin America: Cross-sectional study", American Journal of Obstetrics and Gynecology, vol. 192, No. 2, Feb. 2005, pp. 342-349, doi: 10.1016/j.ajog.2004.10.593.

Contrepois et al., "Optimized Analytical Procedures for the Untargeted Metabolomic Profiling of Human Urine and Plasma by Combining Hydrophilic Interaction (HILIC) and Reverse-Phase Liquid Chromatography (RPLC)—Mass Spectrometry", Molecular & Cellular Proteomics, vol. 14, No. 6, Jun. 2015, pp. 1684-1695, doi: 10.1074/mcp.M114.046508.

Cote et al., "Generation of human monoclonal antibodies reactive with cellular antigens", Proceedings of the National Academy of Sciences, vol. 80, Apr. 1983, pp. 2026-2030, doi: 10.1073/pnas.80.7.2026.

David et al., "Protein iodination with solid state lactoperoxidase", Biochemistry, vol. 13, No. 5, Feb. 1, 1974, pp. 1014-1021, doi: 10.1021/bi00702a028.

\* cited by examiner

Table 1: *Demographics and Birth Characteristics of Discovery and Validation Cohorts*

|  | Discovery N = 21 | Test Set N = 9 |
|---|---|---|
| Maternal age at birth, years | 29.8 ± 3.1 | 29.7 ± 3.3 |
| Gestational age at birth, days | 281 ± 8.4 | 280.7 ± 8.3 |
| No. of subjects with natural labour onset | 12 | 6 |
| No. of subjects with intervention before natural labour onset | 9 | 3 |
| No. of observations per subject, range (median) | 12–33 (24) | 24–36 (25) |

Table 2: A summary of the results of various approaches for predicting gestational age.

| | Cross-validation MAE on training set (N = 21) | | MAE on validation set (N = 9) | |
|---|---|---|---|---|
| | Boosted trees, aligned | Principal Curves | Boosted trees, aligned | Principal curves |
| Using full feature set, all visits ($p = 9,651$) | 1.20 (n = 508) | 1.25 (n = 508) | 1.13 (n = 245) | 0.83 (n = 245) |
| Using compounds features, all visits ($p = 264$) | 1.34 (n = 508) | 1.56 (n = 508) | 1.39 (n = 245) | 0.95 (n = 245) |
| Using full feature set, 3 visits per subject ($p = 9,651$) | 0.93 (n = 55) | 1.07 (n = 55) | 0.88 (n = 27) | 1.20 (n = 27) |
| Using compounds features, 3 visits per subject ($p = 264$) | 0.86 (n = 55) | 1.90 (n = 55) | 1.28 (n = 27) | 1.77 (n = 27) |
| Using top 3 features, 3 visits per subject ($p = 3$) | 1.26 (n = 55) | 1.67 (n = 55) | 1.57 (n = 27) | 1.70 (n = 27) |

Fig. 8

Table 3: *Predicting gestational age on validation set, all visits, using full feature set (N = 9, n = 245, p = 9,651)*

| | Original (LASSO) | Boosted Trees (No Alignment) | Boosted Trees (Aligned) | Principal Curves |
|---|---|---|---|---|
| MAE (weeks) | 2.11 | 1.50 | 1.13 | 0.83 |
| RMSE (weeks) | 2.76 | 2.11 | 1.64 | 1.18 |

Table 4: 21-fold cross-validation on training set for gestational age, all visits, using full feature set (N = 21, n = 508, p = 9,651).

|  | Boosted Trees (No Alignment) | Boosted Trees (Aligned) | Principal Curves |
|---|---|---|---|
| MAE (weeks) | 1.69 | 1.20 | 1.25 |
| RMSE (weeks) | 2.22 | 1.57 | 1.69 |

Table 5: *Predicting gestational age on validation set, all visits, using compounds features (N = 9, n = 245, p = 264.)*

|  | Original (Lasso) | Boosted Trees (No Alignment) | Boosted Trees (Aligned) | Principal Curves |
|---|---|---|---|---|
| MAE (weeks) | 2.81 | 2.01 | 1.59 | 0.95 |
| RMSE (weeks) | 4.14 | 2.63 | 1.89 | 1.28 |

Table 6: Predicting gestational age on validation set, 3 visits per subject, using full feature set (N = 9, n = 27, p = 9,051)

|  | Original (Lasso) | Boosted Trees (No Alignment) | Boosted Trees (Aligned) | Principal Curves |
|---|---|---|---|---|
| MAE (weeks) | 2.18 | 1.32 | 0.88 | 1.20 |
| RMSE (weeks) | 2.70 | 1.70 | 1.12 | 1.01 |

Table 7: 21-fold cross-validation on training set for gestational age, 3 visits per subject, using full feature set ($N = 21$, $n = 55$, $p = 9,051$)

|  | Boosted Trees (No Alignment) | Boosted Trees (Aligned) | Principal Curves |
|---|---|---|---|
| MAE (weeks) | 1.55 | 0.93 | 1.67 |
| RMSE (weeks) | 2.03 | 1.21 | 1.97 |

Table 9. Predicting gestational age on validation set, 3 visits per subject, using compounds features (N = 9, n = 27, p = 264)

| | Lasso | Boosted Trees (No Alignment) | Boosted Trees (Aligned) | Principal Curves |
|---|---|---|---|---|
| MAE (weeks) | 3.05 | 2.07 | 1.28 | 1.77 |
| RMSE (weeks) | 3.72 | 2.67 | 1.61 | 2.43 |

Table 10: *Predicting gestational age on validation set, 3 visits per subject, using top 3 features (N = 9, n = 27, p = 3)*

|  | Lasso | Boosted Trees (No Alignment) | Boosted Trees (Aligned) | Principal Curves |
|---|---|---|---|---|
| MAE (weeks) | 2.82 | 2.32 | 1.57 | 1.76 |
| RMSE (weeks) | 3.67 | 2.91 | 1.82 | 2.17 |

Fig. 25

Table 8: A summary of the results of various approaches for predicting weeks to delivery.

| | Cross-validation MAE on training set ($N = 12$) | | MAE on validation set ($N = 6$) | |
|---|---|---|---|---|
| | Boosted trees, aligned | Principal Curves | Boosted trees, aligned | Principal curves |
| Using full feature set, all visits ($p = 9,651$) | 1.66 ($n = 285$) | 1.65 ($n = 285$) | 1.62 ($n = 159$) | 1.36 ($n = 159$) |
| Using compounds features, all visits ($p = 264$) | 1.71 ($n = 285$) | 2.11 ($n = 285$) | 1.84 ($n = 159$) | 1.81 ($n = 159$) |
| Using full feature set, 3 visits per subject ($p = 9,651$) | 1.54 ($n = 32$) | 2.08 ($n = 32$) | 1.51 ($n = 18$) | 1.47 ($n = 18$) |
| Using compounds features, 3 visits per subject ($p = 264$) | 1.38 ($n = 32$) | 3.00 ($n = 32$) | 1.50 ($n = 18$) | 2.07 ($n = 18$) |
| Using top 3 features, 3 visits per subject ($p = 3$) | 1.54 ($n = 32$) | 1.80 ($n = 32$) | 1.08 ($n = 18$) | 1.65 ($n = 18$) |

Table 11: Predictions for weeks to delivery on validation set, all visits, using full feature set ($N = 6$, $n = 159$, $p = 9,651$)

|  | Lasso | Boosted Trees (No Alignment) | Boosted Trees (Aligned) | Principal Curves |
|---|---|---|---|---|
| MAE (weeks) | 2.37 | 1.90 | 1.62 | 1.36 |
| RMSE (weeks) | 3.08 | 2.50 | 2.25 | 1.99 |

Table 12: *Predicting weeks to delivery, validation set* ($N = 6, n = 18$)

|  | Lasso | Boosted Trees (No Alignment) | Boosted Trees (Aligned) | Principal Curves |
|---|---|---|---|---|
| MAE (weeks) | 2.55 | 1.42 | 1.51 | 1.47 |
| RMSE (weeks) | 3.34 | 1.92 | 1.95 | 2.21 |

Table 13: *Predicting weeks to delivery on validation set, all visits, using compounds features (N = 6, n = 159, p = 264)*

|  | Lasso | Boosted Trees (No Alignment) | Boosted Trees (Aligned) | Principal Curves |
|---|---|---|---|---|
| MAE (weeks) | 2.78 | 2.06 | 1.84 | 1.81 |
| RMSE (weeks) | 3.56 | 2.64 | 2.44 | 2.24 |

Table 14: *Predicting weeks to delivery on validation set, 3 visits per subject, using compounds features* ($N = 6$, $n = 18$, $p = 264$)

| | Lasso | Boosted Trees (No Alignment) | Boosted Trees (Aligned) | Principal Curves |
|---|---|---|---|---|
| MAE (weeks) | 4.10 | 1.80 | 1.80 | 2.07 |
| RMSE (weeks) | 3.08 | 2.24 | 1.99 | 2.46 |

Table 15: *Predicting weeks to delivery on validation set, 3 visits per subject, using top 3 features (N = 6, n = 18, p = 3)*

|  | Lasso | Boosted Trees (No Alignment) | Boosted Trees (Aligned) | Principal Curves |
|---|---|---|---|---|
| MAE (weeks) | 2.89 | 1.57 | 1.08 | 1.65 |
| RMSE (weeks) | 4.03 | 2.08 | 1.39 | 2.11 |

SYSTEMS AND TEMPORAL ALIGNMENT METHODS FOR EVALUATION OF GESTATIONAL AGE AND TIME TO DELIVERY

CROSS REFERENCE TO RELATED APPLICATIONS

This application claims priority to U.S. Provisional Application Ser. No. 63/110,872, entitled "Temporal Alignment Methods for Evaluation of Gestational Progress and Preterm Abortion," filed Nov. 6, 2020, which is incorporated herein by reference in its entirety.

TECHNICAL FIELD

The disclosure is generally directed to processes to evaluate gestational progress and applications thereof, and more specifically to methods that align temporal data to build a computational model for evaluating gestational age, time to labor, preterm birth, and preterm abortion including diagnostics to be utilized for clinical interventions.

BACKGROUND

Pregnancy is one of the most critical periods for mother and child. It involves a tremendous flow of physiological changes and metabolic adaptations week by week, and even small deviations from the norm may have detrimental consequences. There are 300,000 pregnancy and birth-related maternal deaths and 7.5 million perinatal deaths annually worldwide. In addition, 30% of all pregnancies end in miscarriage (<20 weeks), and preterm birth (<37 weeks). The latter is the leading cause of global neonatal morbidity and mortality and is observed for 7-17% of all pregnancies. With 170 million pregnancies yearly worldwide, even small improvements in obstetric health care, based on a better understanding of how pregnancy is regulated, may impact on the wellbeing of a large number of women and children.

Although ultrasound is used in clinics for estimating the gestational age, its accuracy is suboptimal with only 40% of the newborns delivered within 7 days of the predicted due dates. The accuracy is also decreased after the first trimester. Thus, there remains a need in the art for improved methods of estimating gestational age and predicting time to delivery and labor onset.

SUMMARY

Various embodiments are directed towards systems and methods for assessing gestational age and time to delivery. In various embodiments, a trained computational model utilizes measurements of metabolites derived from a pregnant individual to determine gestational progress or time to delivery. In various embodiments, the computational model is trained utilizing temporally aligned analyte measurements derived from a cohort of pregnant individuals. In various embodiments, to determine gestational age, metabolites are extracted from the pregnant individual at one or more timepoints and measured. In various embodiments, the measurements of extracted metabolites are utilized within the trained computational model to determine gestational age.

In an embodiment, gestational age or time to delivery is determined. A biological sample of a pregnant individual is collected at each time point of one or more timepoints. Analytes of the one or more biological samples is measured. A gestation or time to delivery of the pregnant individual is determined via a computational model and the one or more analyte measurements. The computational model has been trained utilizing temporally aligned data features.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 8 provides a table summarizing the results of various approaches for predicting gestational age, generated in accordance with various embodiments.

FIG. 25 provides a table summarizing the results of various approaches for predicting time to gestation, generated in accordance with various embodiments.

DETAILED DESCRIPTION

Turning now to the drawings and data, systems and methods to determine gestational progress based on temporal alignment of analyte measurements derived from a pregnant individual and applications thereof in accordance with various embodiments are described. In various embodiments, gestational progress is a gestational age and/or a time to delivery. In some embodiments, biological samples (e.g., blood draw) are collected from a pregnant individual at one or more timepoints and particular analytes within each biological sample are measured. In some embodiments, the analyte measurements are used to compute gestational progress via a computational model that was trained accounting for the temporal difference in the acquisition of analytes. It has been found that temporally aligning analyte data based on the temporal differences improves training of a model to predict gestational progress, providing an accurate indication of an individual's pregnancy timeline. Many embodiments utilize an individual's gestational age or time to delivery to perform further diagnostic testing and/or treat the individual. In some instances, a diagnostic can include medical imaging (e.g., ultrasonography), periodic medical checkups, fetal monitoring, blood tests (e.g., glucose), microbial culture tests, genetic screening, chorionic villus sampling, and amniocentesis. In some instances, a treatment can include a medication, a dietary supplement, Caesarian delivery, a surgical procedure, and any combination thereof.

Many treatment regimens and clinical decisions in obstetrics depend on an accurate estimation of the timing and progression of pregnancy. Current clinical determination of gestational age and due date are typically based on information about last menstruation date or ultrasound imaging, which can be imprecise. An accurate and cost-effective method for estimating gestational age and delivery time is in need.

Temporal Analysis of Analytes Indicative of Gestational Progress

Figure 1:
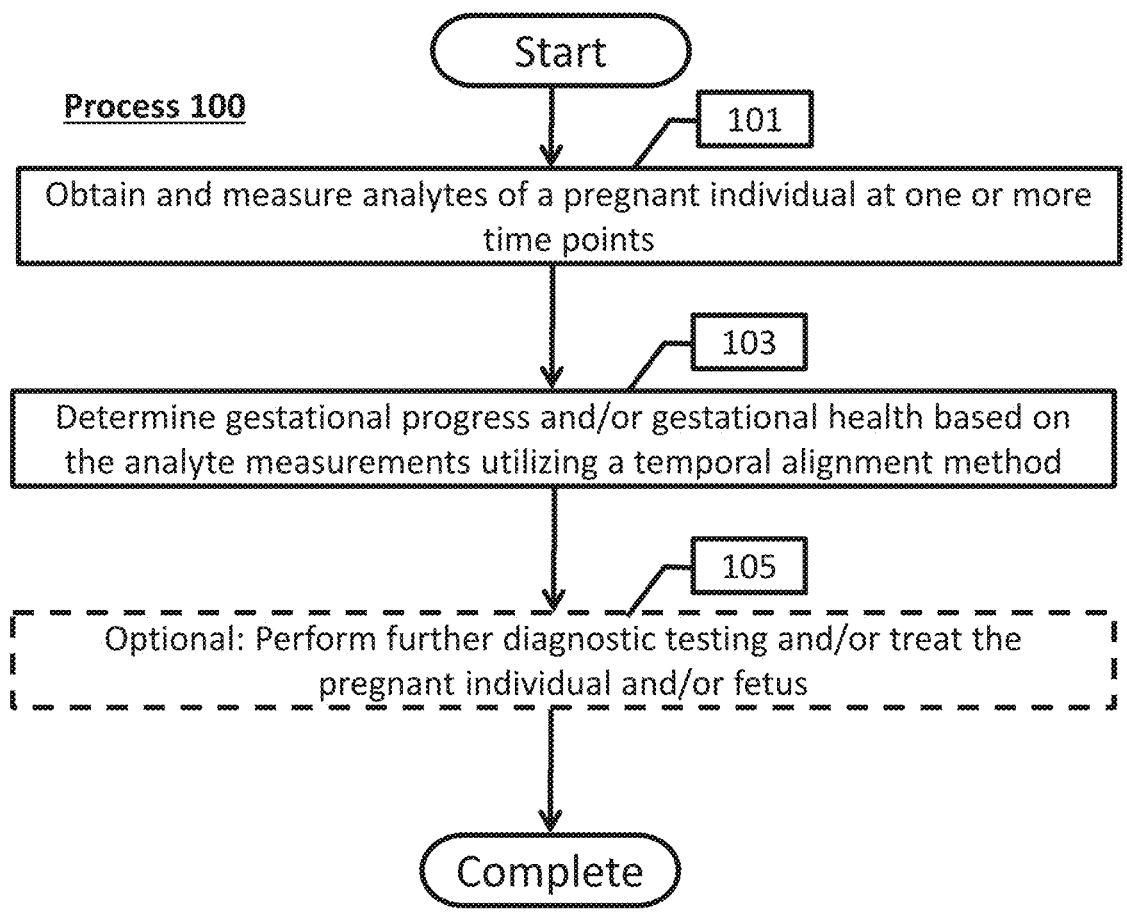
FIG. 1 provides a process for performing diagnostics and/or treating a pregnant individual based on their analyte data in accordance with various embodiments.

A process for determining pregnancy progress, gestational age, and/or time to delivery, using analyte measurements and temporal alignment of those measurements, in accordance with various embodiments, is shown in FIG. 1. The process to determines an indication of gestational progress, which can be utilized to perform further diagnostics and/or treat an individual. For example, this process can be used to accurately determine the gestational progress of a pregnant individual without the need for sonography.

In a number of embodiments, analytes and analyte measurements are clinical and molecular constituents and measurements that can be captured in medical and/or laboratory setting and are to include metabolites, protein constituents, genomic DNA, transcript expression, and lipids. In some embodiments, metabolites are to include intermediates and products of metabolism such as (for example) sugars, amino acids, nucleotides, antioxidants, organic acids, polyols, vitamins, and the like. In various embodiments, protein constituents are chains of amino acids which are to include (but not limited to) peptides, enzymes, receptors, ligands, antibodies, transcription factors, cytokines, hormones, growth factors and the like. In some embodiments, genomic DNA is DNA of an individual and includes (but is not limited to) copy number variant data, single nucleotide variant data, polymorphism data, mutation analysis, insertions, deletions, epigenetic data and partial and full genomes. In various embodiments, transcript expression is the evidence of RNA molecules of a particular gene or other RNA transcripts, and is to include (but not limited to) analysis of expression levels of particular transcript targets, splicing variants, a class or pathway of gene targets, and partial and full transcriptomes. In some embodiments, lipids are a broad class of molecules that include (but are not limited to) fatty acid molecules, fat soluble vitamins, glycerolipids, phospholipids, sterols, sphingolipids, prenols, saccharolipids, polyketides, and the like.

In some embodiments, clinical data and/or personal data can be additionally used to indicate gestation age and/or health. In some embodiments, clinical data is to include medical patient data such as (for example) weight, height, heart rate, blood pressure, body mass index (BMI), clinical tests and the like. In various embodiments, personal data is to include data captured by an individual such as (for example) wearable data, physical activity, diet, substance abuse and the like.

Referring back to FIG. 1, process 100 begins with obtaining and measuring (101) analytes from a pregnant individual at one or more timepoints. In many instances, analytes are measured from a blood extraction, stool sample, urine sample, saliva or biopsy. In some embodiments, an individual's sample is collected during fasting, or in a controlled clinical assessment. A number of methods are known to collect samples from an individual and can be used within various embodiments. In some of these embodiments, analytes are measured with periodicity (e.g., weekly, monthly, trimester).

In a number of embodiments, an individual is any individual that has their analytes extracted and measured, especially individuals that have an indication of pregnancy. In some embodiments, an individual has been diagnosed as being pregnant (e.g., as determined by urine test or ultrasound). Embodiments are also directed to an individual that has not yet been diagnosed as pregnant.

A number of analytes can be used to indicate gestation age and/or health, including (but not limited to) metabolites, protein constituents, genomic DNA, transcript expression, and lipids. In some embodiments, clinical data and/or personal data can be additionally used to indicate gestation age and/or health. Analytes can be detected and measured by a number of methods, including nucleic acid and protein sequencing, mass spectrometry, colorimetric analysis, immunodetection, and the like.

In several embodiments, analyte measurements are performed by taking one or more time-point measurements. In some embodiments in which a plurality of measurements is taken, the temporal difference between the measurement time points is utilized to help align the measurements. A number of embodiments utilize a computational model that incorporates analyte measurements, such as a supervised regression model or principles curve model. Significance can be determined by calculating p-values and/or contribution, which may be corrected for multiple hypotheses testing. It should be noted however, that there are several computational models and statistical methods that can utilize analyte measurements and may also fall within some.

In a number of embodiments, dynamic correlations use a ratio of analyte measurements between two time points, a percent change of analyte measurements over a period of time, a rate of change of analyte measurements over a period of time, or any combination thereof. Several other dynamic measurements may also be used in the alternative or in combination in accordance with multiple embodiments.

Using analyte measurements collected at a plurality of time points and a temporal alignment method, process 100 determines (103) gestational progress based on the analyte measurements and the temporal alignment of sampling time points. In many embodiments, a computational model that incorporates temporal differences between sampling time points is used to indicate gestational progress and/or. It has been found that prediction of gestational progress improves when a plurality of predictions for a single individual are aligned using the difference in sampling times. In several embodiments, modeling gestational progress is used to substitute other gestational tests, such as (for example) ultrasonography. In various embodiments, measurements of analytes can be used as a precursor indicator to determine whether to perform a further clinical test, such as (for example) ultrasonography.

Having determined an individual's gestational progress, further diagnostic test can be performed or the pregnant individual and/or fetus can be treated (105). In some instances, a diagnostic can include medical imaging (e.g., ultrasonography), periodic medical checkups, fetal monitoring, blood tests (e.g., glucose), microbial culture tests, genetic screening, chorionic villus sampling, amniocentesis, and any combination thereof. In some instances, a treatment can include a medication, a dietary supplement, Caesarian delivery, a surgical procedure, and any combination thereof. Medications include (but are not limited to) progesterone, androstatne-3,17-diol, estriol-16-glucuronide, and dehydroisoandrosterone sulfate. For more details on potential therapeutics, see international patent application PCT/US2020/052311, the disclosure of which is incorporated herein by reference.

While specific examples of determining an individual's gestational progress utilizing temporal alignment are described above, one of ordinary skill in the art can appreciate that various steps of the process can be performed in different orders and that certain steps may be optional according to some embodiments. As such, it should be clear that the various steps of the process could be used as appropriate to the requirements of specific applications. Furthermore, any of a variety of processes for determining an individual's gestational progress appropriate to the requirements of a given application can be utilized in accordance with various embodiments.

Modeling Gestational Progress with Temporal Alignment

Figure 2:
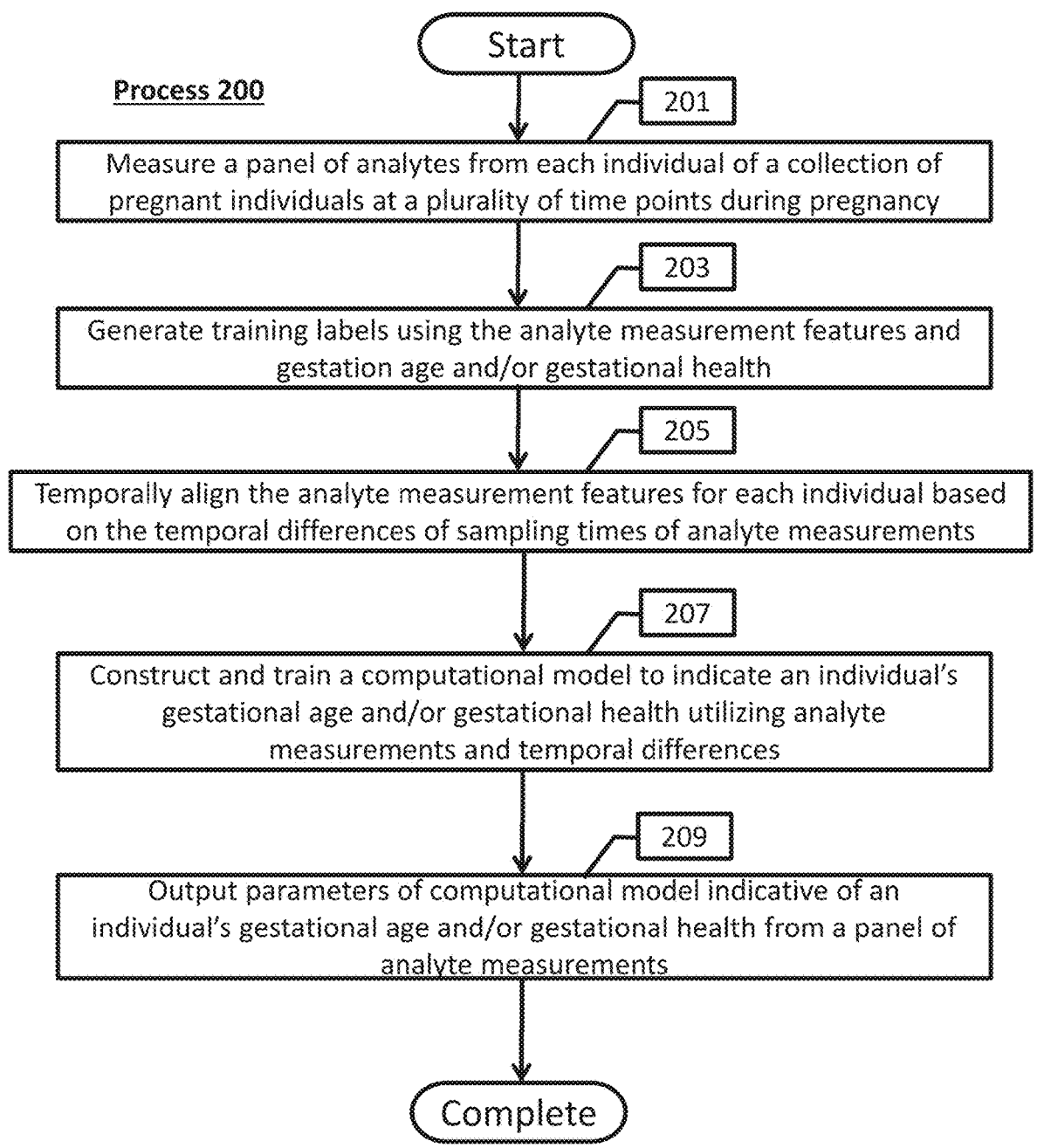
FIG. 2 provides a process to construct and train a computational model to determine a pregnant individual's gestational progress in accordance with accordance with various embodiments.

A process for constructing and training a computational model to indicate gestational progress based on temporally aligned feature data, in accordance with various embodiments, is shown in FIG. 2. Process 200 measures (201) a panel of analytes from each individual of a collection of pregnant individuals at a plurality of time points during pregnancy. In several embodiments, analytes are measured from a blood sample, stool sample, urine sample, saliva or biopsy of an individual. In some embodiments, an individual's sample is collected during fasting. A number of methods are known to extract samples from an individual and can be used within various embodiments. In several embodiments, analytes are extracted and measured at each time point, resulting in a dynamic analysis of the analytes.

In several embodiments, analytes are collected with periodicity across the timeline of pregnancy and postpartum. Accordingly, in some embodiments, analyte measurements are performed weekly, bi-weekly, monthly, per trimester, pre- and post-health event, after delivery, and any combination thereof. The precise extraction timeline will depend on the data to be collected and the model to be constructed.

A number of analytes can be used as features within a computational model to determine gestational progress, including (but not limited to) metabolites, protein constituents, genomic DNA, transcript expression, and lipids. In some embodiments, clinical data and/or personal data can be additionally used as data features. Analytes can be detected and measured by a number of methods, including nucleic acid and protein sequencing, mass spectrometry, colorimetric analysis, immunodetection, and the like.

A collection of individuals, in accordance with many embodiments, is a group of pregnant individuals that have had their analytes collected and measured so that their data can be used to construct and train a computational model. A collection will typically include individuals that are diagnosed as pregnant such that their analytes can be extracted along the pregnancy timeline. The number of individuals in a collection can vary, and in some embodiments, having a greater number of individuals will increase the prediction power of a trained computer model. The precise number and composition of individuals will vary, depending on the model to be constructed and trained.

Using the analyte measurements and gestational progress, process 200 generates (203) training labels that provide a correspondence between analyte measurement features and gestational progress. For training purposes, in various embodiments, gestational progress is determined via sonography. In several embodiments, analyte measurements used to generate training labels are determinative of gestational progress. In some embodiments, analyte measurements are standardized.

Based on studies performed, it has been found that several analyte measurements provide robust predictive ability, including (but not limited to) metabolites, protein constituents, genomic DNA, transcript expression, and lipids. A number of methods can be used to select analyte measurements to be used as features in the training model. In some embodiments, correlation measurements between analyte measurements and gestational progress are used to select features. In various embodiments, a computational model is used to determine which analyte measurements are best predictors. For example, a linear regression model (e.g., boosted trees) or principal curve model can be used to determine which analyte measurement features provide the best predictive power as determined by their contribution.

It has been found that the following 30 metabolites provide predictive power and one or more of these metabolites can be utilized within a predictive model: N,N'-Dicarbobenzyloxy-L-ornithine, 1-(1Z-Hexadecenyl)-sn-glycero-3-phosphoethanolamine (PE(P-16:0e/0:0)), delta4-Dafachronic acid, $C_{29}H_{36}O_9$, 7alpha,24-Dihydroxy-4-cholesten-3-one, $C_{22}H_{43}O_{12}P$, $C_{27}H_{44}O_9$, $C_{19}H_{28}O_7S$, Androstane-3,17-diol, 21-Hydroxypregnenolone, Estriol-16-Glucuronide, $C_{25}H_{40}O_9$, $C_{27}H_{44}O_4$, $C_{27}H_{42}O_3$, bilobol, [1-(3,5-dihydroxyphenyl)-12-hydroxytridecan-2-yl] acetate, $C_{26}H_{52}NO_8P$, $C_{27}H_{42}O_8$, Prolylphenylalanine, N,N,Diacetyl-Lys-DAla-DAla, $C_{23}H_{49}N_2O_5P$, $C_{21}H_{29}O$, $C_{33}H_{53}O_9$, $C_{22}H_{35}O_3$, $C_{30}H_{44}NO_3S$, 1,1'-(1,8-dioxo-1,8-octanediyl)bis[glycyl-glycine], $C_{27}H_{42}O_{10}$, 6-ketoestriol sulfate, DAH-3-Keto-4-en, and Progesterone. It is noted that two variations of progesterone, as detected mass spectrometry, were found to be predictive: progesterone (m/z: 315, RT/min: 9.3) and progesterone (m/z 337, RT/min 9.3). In addition, 11 more metabolites unable to labeled by detectable by mass spectrometry were found to be predictive: (m/z: 511, RT/min: 5.4), (m/z: 519, RT/min: 8.6), (m/z: 563, RT/min: 6.6), (m/z: 353, RT/min: 7.9), (m/z: 487, RT/min: 6.6), (m/z: 319, RT/min: 2.6), (m/z: 821, RT/min: 9.1), (m/z: 653, RT/min: 9.3), (m/z: 798, RT/min: 8.5), (m/z: 260, RT/min: 9.8), and (m/z: 823, RT/min: 9.3). Likewise, it has been found that the following 42 protein constituents provide predictive power and one or more can used in a predictive model: NTRK2, LAIR2, CD200R1, LXN, DRAXIN, ROBO2, CD93, NTRK3, MDGA1, CRTAM, IL12B/IL12A, RGMA, IL2RA, ESM1, FcRL2, UPAR, MCP2, IL5Ralpha, CLM1, uPA, CCL28, PCSK9, PDGFRalpha, SMPD1, SKR3, DLK1, NRP2, MSR1, GMCSFRalpha, CTSC, RET, SMOC2, PRTG, PVRL4, ST2, NrCAM, SYND1, TNFRSF12A, DDR1, CD200, GRN, and PAI1. Based on the foregoing, it should be understood that a number of analyte features can be used solitarily or combined in any fashion to train a predictive computational model.

Process 200 also temporally aligns (205) the analyte measurement features of each individual in the collection of individuals based on the temporal differences between the plurality of sampling time points of analyte measurements. Because each individual within the collection had their analytes collected at a plurality of sampling time points, the temporal difference between each sampling time point can be determined. Each set of analyte measurements for a particular time point is paired with the determined gestational age (e.g., as determined by sonography) to yield a series of data pairs. For example, a pregnant individual can have her analytes collected and measured at 8 weeks, 15 weeks, 17 weeks, and 20 weeks resulting in 4 temporally spaced data pairs for each analyte measurement. Each data pair is a vector that can be used as a feature to train a computational model. Further, the difference in sampling time is known. Returning back to the example of analytes collected and measured at 8 weeks, 15 weeks, 17 weeks, and 20 weeks, the temporal differences would be known between the vectors (e.g., 7 weeks between 8 and 15). For more description of an example of temporal alignment, see the Exemplary Embodiments.

Training labels associating analyte measurement features and gestational progress and the temporal differences are used to construct and train (207) a computational model to determine an individual's gestational progress. Various embodiments construct and train a model to determine the individual's pregnancy progression and/or time to delivery. A number of models can be used in accordance with various embodiments, including (but not limited to) ridge regression, K-nearest neighbors, LASSO regression, elastic net, least angle regression (LAR), random forest, gradient boosted trees, and principal components analysis. In many embodiments, the temporal information is used to improve the predictions from the standard model utilizing the known difference between the sampling time points. In some embodiments, estimates of the standard model are combined to borrow strength across different collected samples for a given pregnant individual. For further details on an example of aligning prediction intervals, see the Exemplary Embodiments.

In some embodiments of models, a timeline is a full gestational timeline (i.e., from first missed menstruation or fertilization to birth) or a partial gestational timeline (e.g., first trimester, second trimester, third trimester). Various embodiments include postpartum analyte data and thus a timeline would include postpartum periods as well. It should be understood that any appropriate time period can be utilized in accordance with various embodiments.

In several embodiments, a computational model incorporates analyte data of individuals at particular time points of a pregnancy timeline (e.g., 4 weeks, 6 weeks, 8 weeks, 10 weeks, 12 weeks 16 weeks, 24 weeks, 28 weeks, 32 weeks, 36 weeks or 40 weeks). In some embodiments, sampling time points are in relation to the time to birth (e.g., 1 week, 2 weeks, 3 weeks, 4 weeks, 6 weeks, or 8 weeks to birth).

Models and sets of training labels used to train a model can be evaluated for their ability to accurately determine gestational progress. By evaluating models, predictive abilities of analyte measurements can be confirmed. In some embodiments, a portion of the cohort data is withheld to test the model to determine its efficiency and accuracy. A number of accuracy evaluations can be performed, including (but not limited to) area under the receiver operating characteristics (AU ROC), R-square error analysis, and mean square error analysis. In some embodiments, the contribution of each feature to the ability to predict outcome is determined. In some embodiments, top contributing features are utilized to construct the model. Accordingly, an optimized model can be identified.

Process 200 also outputs (209) the parameters of a computational model indicative of an individual's gestational age from a panel of analyte measurements. Computational models can be used to determine an individual's gestational progress, provide diagnoses, and treat an individual accordingly, as will be described in detail below.

While specific examples of processes for constructing and training a computational model utilizing temporal alignment to determine an individual's gestational progress are described above, one of ordinary skill in the art can appreciate that various steps of the process can be performed in different orders and that certain steps may be optional according to some embodiments. As such, it should be clear that the various steps of the process could be used as appropriate to the requirements of specific applications. Furthermore, any of a variety of processes for constructing and training a computational model appropriate to the requirements of a given application can be utilized in accordance with various embodiments.

Figure 3:
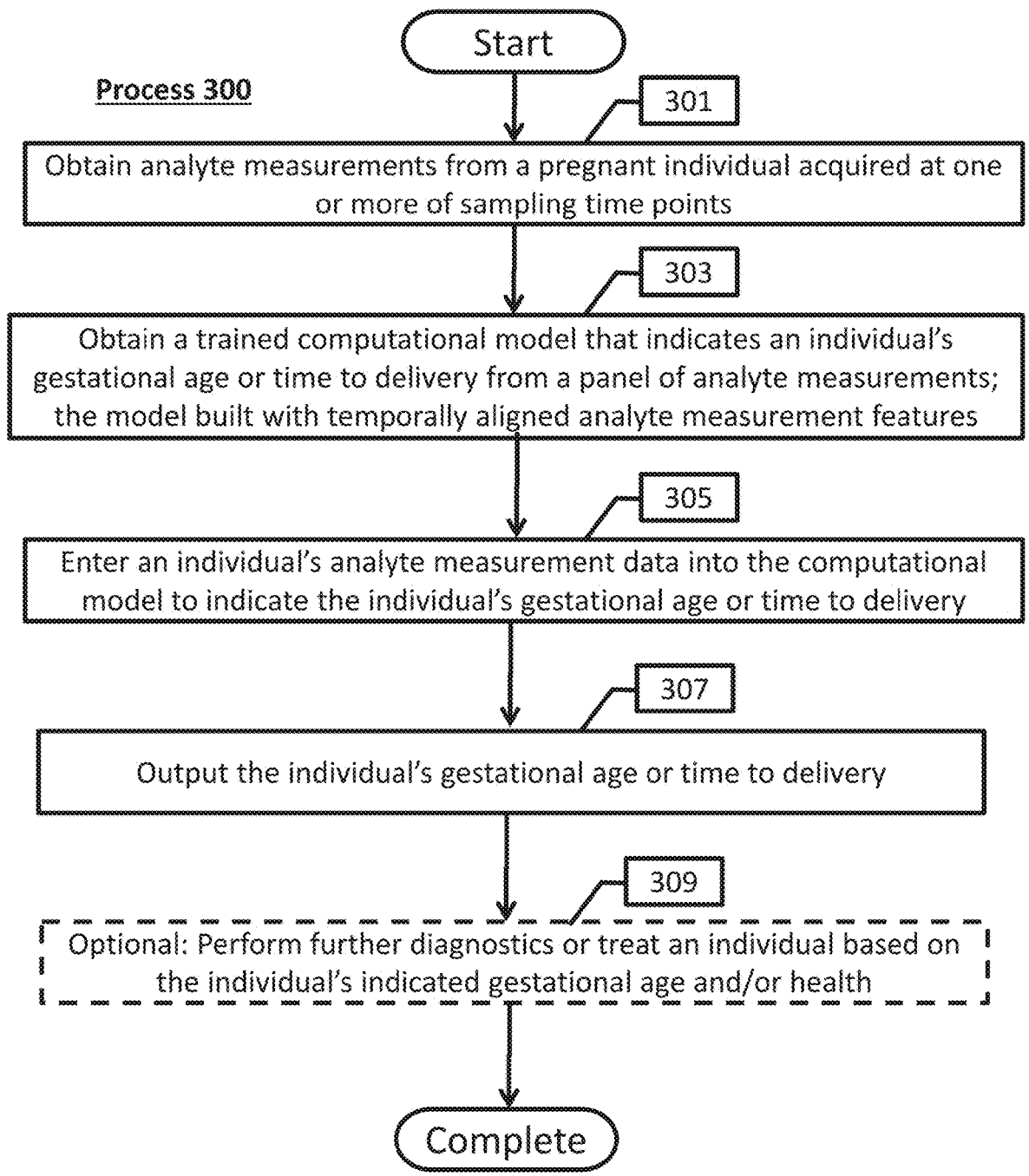
FIG. 3 provides a process to perform a diagnostic and/or treat a pregnant individual based on the individual's computed indication of gestational progress in accordance with various embodiments.

Determination of an Individual's Pregnancy Progression and Potential Complications Using Analyte Measurements Once a computational model has been constructed and trained, it can be used to compute a determination of an individual's gestational progress. As shown in FIG. 3, a method to determine an individual's gestational progress using a trained computational model is provided in accordance with an embodiment. Process 300 obtains (301) analyte measurements from a pregnant individual acquired at one or more sampling time points. In some embodiments, the temporal difference between sampling time points is known. In some embodiments, the gestation age at the time sample acquisition is unknown.

In several embodiments, analytes are measured from a blood sample, stool sample, urine sample, saliva or biopsy of an individual. In some embodiments, an individual's samples are collected during fasting. A number of methods are known to extract a sample from an individual and can be used within various embodiments. In some of these embodiments, analytes are measured with periodicity (e.g., weekly, monthly, trimester).

A number of analytes can be used to determine gestational progress, including (but not limited to) metabolites, protein constituents, genomic DNA, transcript expression, and lipids. In some embodiments, clinical data and/or personal data can be additionally used to determine gestational progress. Analytes can be detected and measured by a number of methods, including nucleic acid and protein sequencing, mass spectrometry, colorimetric analysis, immunodetection, and the like. In many embodiments, the precise panel of analytes to be measured depends on the constructed and trained computational model to be used, as the input analyte measurement data that will be needed to at least partially overlap with the features used to train the model. That is, there should be enough overlap between the feature measurements used to train the model and the individual's analyte measurements obtained such that gestational progress can be determined.

Process 300 also obtains (303) a trained computational model that indicates an individual's gestational progress from a panel of analyte measurements in which the model is trained with temporally aligned analyte measurement features. Any computational model that has been trained utilizing temporally aligned analyte data and can compute an indicator of an individual's gestational progress from analyte measurements from one or more extractions can be used. In some embodiments, the computational model is constructed and trained as described in FIG. 2. The computational model, in accordance with various embodiments, has been optimized to accurately and efficiently indicate gestational progress.

A number of models can be used in accordance with various embodiments, including (but not limited to) ridge regression, K-nearest neighbors, LASSO regression, elastic net, least angle regression (LAR), random forest, boosted tress, and principal curves.

Process 300 also enters (305) an individual's analyte measurement data into a computational model to indicate the individual's gestational progress. In some embodiments, the analyte measurement data is used to compute an individual's gestational progress in lieu of performing a traditional gestational analysis (e.g., sonography). Various embodiments utilize the analyte measurement data and computational model in combination with one or more clinical diagnostic methods.

Based on studies performed, it has been found that several analyte measurements provide robust predictive ability, including (but not limited to) particular metabolites, protein constituents, genomic DNA, transcript expression, and lipids. A number of methods can be used to select analyte measurements to be used as features in the training model. In some embodiments, correlation measurements between analyte measurements and gestational progress are used to select features. In various embodiments, a computational model is used to determine which analyte measurements are best predictors. For example, a linear regression model (e.g., LASSO) or elastic net model can be used to determine which analyte measurement features provide the best predictive power as determined by their contribution.

A selection of predictive analyte measurement features is described in the Exemplary Embodiments section. For instance, it has been found that the following 30 metabolites provide predictive power and one or more can be utilized within a predictive model: N,N'-Dicarbobenzyloxy-L-ornithine, 1-(1Z-Hexadecenyl)-sn-glycero-3-phosphoethanolamine (PE(P-16:0e/0:0)), delta4-Dafachronic acid, $C_{29}H_{36}O_9$, 7alpha,24-Dihydroxy-4-cholesten-3-one, $C_{22}H_{43}O_{12}P$, $C_{27}H_{44}O_9$, $C_{19}H_{28}O_7S$, Androstane-3,17-diol, 21-Hydroxypregnenolone, Estriol-16-Glucuronide, $C_{25}H_{40}O_9$, $C_{27}H_{44}O_4$, $C_{27}H_{42}O_3$, bilobol, [1-(3,5-dihydroxyphenyl)-12-hydroxytridecan-2-yl] acetate, $C_{26}H_{52}NO_8P$, $C_{27}H_{42}O_8$, Prolylphenylalanine, N,N,Di-acetyl-Lys-DAla-DAla, $C_{23}H_{49}N_2O_5P$, $C_{21}H_{29}O$, $C_{33}H_{53}O_9$, $C_{22}H_{35}O_3$, $C_{30}H_{44}NO_3S$, 1,1'-(1,8-dioxo-1,8-octanediyl)bis[glycyl-glycine], $C_{27}H_{42}O_{10}$, 6-ketoestriol sulfate, DAH-3-Keto-4-en, and progesterone. It is noted that two variations of progesterone, as detected mass spectrometry, were found to be predictive: progesterone (m/z: 315, RT/min: 9.3) and progesterone (m/z 337, RT/min 9.3). In addition, 11 more metabolites unable to labeled by detectable by mass spectrometry were found to be predictive: (m/z: 511, RT/min: 5.4), (m/z: 519, RT/min: 8.6), (m/z: 563, RT/min: 6.6), (m/z: 353, RT/min: 7.9), (m/z: 487, RT/min: 6.6), (m/z: 319, RT/min: 2.6), (m/z: 821, RT/min: 9.1), (m/z: 653, RT/min: 9.3), (m/z: 798, RT/min: 8.5), (m/z: 260, RT/min: 9.8), and (m/z: 823, RT/min: 9.3). In some embodiments, a gestational progress prediction model utilizes measurements of at least one of the listed metabolites. In some embodiments, a gestational progress prediction model utilizes measurements of at least two of the listed metabolites. In some embodiments, a gestational progress prediction model utilizes measurements of at least three of the listed metabolites. In some embodiments, a gestational progress prediction model utilizes measurements of at least four of the listed metabolites. In some embodiments, a gestational progress prediction model utilizes measurements of at least five of the listed metabolites. In some embodiments, a gestational progress prediction model utilizes measurements of at least six of the listed metabolites. In some embodiments, a gestational progress prediction model utilizes at least measurements of seven of the listed metabolites. In some embodiments, a gestational progress prediction model utilizes measurements of at least eight of the listed metabolites. In some embodiments, a gestational progress prediction model utilizes measurements of at least nine of the listed metabolites. In some embodiments, a gestational progress prediction model utilizes measurements of at least 10 of the listed metabolites. In some embodiments, a gestational progress prediction model utilizes measurements of at least 15 of the listed metabolites. In some embodiments, a gestational progress prediction model utilizes measurements of at least 20 of the listed metabolites. In some embodiments, a gestational progress prediction model utilizes measurements of at least 25 of the listed metabolites. In some embodiments, a gestational progress prediction model utilizes measurements of at least 30 of the listed metabolites.

In one study, it was determined that tetrahydrodeoxycorticosterone (THDOC), estriol-16-glucuronide, and progesterone are high contributors for determining gestational age. Accordingly, various embodiments are directed to a model to predict gestational age or time to delivery that utilizes measurements of one or more of the following analytes: THDOC, estriol-16-glucuronide, and progesterone. In some embodiments, a model to predict gestational age or time to delivery that utilizes measurements of two or more of the following analytes: THDOC, estriol-16-glucuronide, and progesterone. In some embodiments, a model to predict gestational age or time to delivery utilizes measurements of the three following analytes: THDOC, estriol-16-glucuronide, and progesterone.

Process 300 can also output (307) an individual's gestational age and/or time to delivery. Furthermore, based on an individual's indicated gestational progress, the individual is optionally further examined and/or treated (309). In several embodiments, an individual is provided with a personalized treatment plan. Further discussion of treatments that can be utilized in accordance with this embodiment are described in detail below, which may include various medications, dietary supplements, and surgical procedures.

While specific examples of processes for determining an individual's gestational progress utilizing temporally aligned analyte are described above, one of ordinary skill in the art can appreciate that various steps of the process can be performed in different orders and that certain steps may be optional according to some embodiments. As such, it should be clear that the various steps of the process could be used as appropriate to the requirements of specific applications. Furthermore, any of a variety of processes for computing an individual's gestational progress appropriate to the requirements of a given application can be utilized in accordance with various embodiments.

Feature Selection

As explained in the previous sections, analyte measurements are used as features to construct a computational model that is then used to indicate an individual's gestational progress. Analyte measurement features used to train the model can be selected by a number of ways. In some embodiments, analyte measurement features are determined by which measurements provide strong correlation with gestational progress. In various embodiments, analyte measurement features are determined using a computational model, such as Bayesian network, which can determine which analyte measurements influence or are influenced by an individual's gestational progress. Embodiments also consider practical factors, such as (for example) the ease and/or cost of obtaining the analyte measurement, patient comfort when obtaining the analyte measurement, and current clinical protocols are also considered when selecting features.

Correlation analysis utilizes statistical methods to determine the strength of relationships between two measurements. Accordingly, a strength of relationship between an analyte measurement and gestational progress can be determined. Many statistical methods are known to determine correlation strength (e.g., correlation coefficient), including linear association (Pearson correlation coefficient), Kendall rank correlation coefficient, and Spearman rank correlation coefficient. Analyte measurements that correlate strongly with gestational progress can then be used as features to construct a computational model to determine an individual's gestational progress.

In a number of embodiments, analyte measurement features are identified by a computational model, including (but not limited to) a Bayesian network model, LASSO, random boosted trees, and elastic net. In some embodiments, the contribution of a feature to the predictive ability of the model is determined and features are selected based on their contribution. In some embodiments, the top contributing features are utilized. In some embodiments, the features that contribute over a percentage are selected (e.g., each feature that contributes at least 1% or the combination of top features that provide 90% contribution). In various embodiments, features that contribute at least 0.1%, 0.5%, 1%, 2%, 3%, 4%, 5%, or 10% to outcome prediction are selected. In various embodiments, the top features that in combination provide at least 50%, 75%, 80%, 90%, 95%, 99%, 99.5%, or 99.9% to outcome prediction are selected. The precise number of contributing features will depend on the results of the model and each feature's contribution. Various embodiments utilize an appropriate computational model that results in a number of features that is manageable. For instance, constructing predictive models from hundreds to thousands of analyte measurement features may have overfitting issues. On the other hand, too few features can result in less prediction power.

Biomarkers as Indicators of Gestation Age and Health

In several embodiments, biomarkers are detected and measured, and based on the ability to be detected and/or level of the biomarker, gestational progress can be determined directly or via a computational model. Biomarkers that can be used in the practice include (but are not limited to) metabolites, protein constituents, genomic DNA, transcript expression, and lipids. As discussed in the Exemplary embodiments, a number of biomarkers have been found to be useful to determine gestational progress, including (but not limited to) N,N'-Dicarbobenzyloxy-L-ornithine, 1-(1Z-Hexadecenyl)-sn-glycero-3-phosphoethanolamine (PE(P-16:0e/0:0)), delta4-Dafachronic acid, $C_{29}H_{36}O_9$, 7alpha,24-Dihydroxy-4-cholesten-3-one, $C_{22}H_{43}O_{12}P$, $C_{27}H_{44}O_9$, $C_{19}H_{28}O_7S$, Androstane-3,17-diol, 21-Hydroxypregnenolone, Estriol-16-Glucuronide, $C_{25}H_{40}O_9$, $C_{27}H_{44}O_4$, $C_{27}H_{42}O_3$, bilobol, [1-(3,5-dihydroxyphenyl)-12-hydroxytridecan-2-yl] acetate, $C_{26}H_{52}NO_8P$, $C_{27}H_{42}O_8$, Prolylphenylalanine, N,N,Diacetyl-Lys-DAla-DAla, $C_{23}H_{49}N_2O_5P$, $C_{21}H_{29}O$, $C_{33}H_{53}O_9$, $C_{22}H_{35}O_3$, $C_{30}H_{44}NO_3S$, 1,1'-(1,8-dioxo-1,8-octanediyl)bis[glycyl-glycine], $C_{27}H_{42}O_{10}$, 6-ketoestriol sulfate, DAH-3-Keto-4-en, and Progesterone. It is noted that two variations of progesterone, as detected mass spectrometry, were found to be predictive: progesterone (m/z: 315, RT/min: 9.3) and progesterone (m/z 337, RT/min 9.3) (see Table 3). In addition, 11 more metabolites unable to labeled by detectable by mass spectrometry were found to be predictive: (m/z: 511, RT/min: 5.4), (m/z: 519, RT/min: 8.6), (m/z: 563, RT/min: 6.6), (m/z: 353, RT/min: 7.9), (m/z: 487, RT/min: 6.6), (m/z: 319, RT/min: 2.6), (m/z: 821, RT/min: 9.1), (m/z: 653, RT/min: 9.3), (m/z: 798, RT/min: 8.5), (m/z: 260, RT/min: 9.8), and (m/z: 823, RT/min: 9.3). In addition, a number of protein constituent biomarkers have been found to be useful to determine gestational progress, including (but not limited to) NTRK2, LAIR2, CD200R1, LXN, DRAXIN, ROBO2, CD93, NTRK3, MDGA1, CRTAM, IL12B/IL12A, RGMA, IL2RA, ESM1, FcRL2, UPAR, MCP2, IL5Ralpha, CLM1, uPA, CCL28, PCSK9, PDGFRalpha, SMPD1, SKR3, DLK1, NRP2, MSR1, GMCSFRalpha, CTSC, RET, SMOC2, PRTG, PVRL4, ST2, NrCAM, SYND1, TNFRSF12A, DDR1, CD200, GRN and PAI1.

Detecting and Measuring Levels of Biomarkers

Analyte biomarkers in a biological sample (e.g., blood extraction, stool sample, urine sample, saliva, or biopsy) can be determined by a number of suitable methods. Suitable methods include chromatography (e.g., high-performance liquid chromatography (HPLC), gas chromatography (GC), liquid chromatography (LC)), mass spectrometry (e.g., MS, MS-MS), NMR, enzymatic or biochemical reactions, immunoassay, and combinations thereof. For example, mass spectrometry can be combined with chromatographic methods, such as liquid chromatography (LC), gas chromatography (GC), or electrophoresis to separate the metabolite being measured from other components in the biological sample. See, e.g., Hyotylainen (2012) Expert Rev. Mol. Diagn. 12(5):527-538; Beckonert et al. (2007) Nat. Protoc. 2(11): 2692-2703; O'Connell (2012) Bioanalysis 4(4):431-451; and Eckhart et al. (2012) Clin. Transl. Sci. 5(3):285-288; the disclosures of which are herein incorporated by reference. Alternatively, analytes can be measured with biochemical or enzymatic assays. For example, glucose can be measured with a hexokinase-glucose-6-phosphate dehydrogenase coupled enzyme assay. In another example, biomarkers can be separated by chromatography and relative levels of a biomarker can be determined from analysis of a chromatogram by integration of the peak area for the eluted biomarker.

Immunoassays based on the use of antibodies that specifically recognize a biomarker may be used for measurement of biomarker levels. Such assays include (but are not limited to) enzyme-linked immunosorbent assay (ELISA), radioimmunoassays (RIA), "sandwich" immunoassays, fluorescent immunoassays, enzyme multiplied immunoassay technique (EMIT), capillary electrophoresis immunoassays (CEIA), immunoprecipitation assays, western blotting, immunohistochemistry (IHC), flow cytometry, and cytometry by time of flight (CyTOF).

Antibodies that specifically bind to a biomarker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). A biomarker antigen can be used to immunize a mammal, such as a mouse, rat, rabbit, guinea pig, monkey, or human, to produce polyclonal antibodies. If desired, a biomarker antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface-active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a biomarker antigen can be prepared using any technique which provides for the production of antibody molecules by continuous cell lines in culture. These techniques include, but are not limited to, the hybridoma technique, the human B cell hybridoma technique, and the EBV hybridoma technique (Kohler et al., Nature 256, 495-97, 1985; Kozbor et al., J. Immunol. Methods 81, 31 42, 1985; Cote et al., Proc. Natl. Acad. Sci. 80, 2026-30, 1983; Cole et al., Mol. Cell Biol. 62, 109-20, 1984).

In addition, techniques developed for the production of "chimeric antibodies," the splicing of mouse antibody genes to human antibody genes to obtain a molecule with appropriate antigen specificity and biological activity, can be used (Morrison et al., Proc. Natl. Acad. Sci. 81, 6851-55, 1984; Neuberger et al., Nature 312, 604-08, 1984; Takeda et al., Nature 314, 452-54, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332. Human monoclonal antibodies can be prepared in vitro as described in Simmons et al., PLoS Medicine 4(5), 928-36, 2007.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (Burton, Proc. Natl. Acad. Sci. 88, 11120-23, 1991).

Single-chain antibodies also can be constructed using a DNA amplification method, such as PCR, using hybridoma cDNA as a template (Thirion et al., Eur. J. Cancer Prev. 5, 507-11, 1996). Single-chain antibodies can be mono- or bispecific, and can be bivalent or tetravalent. Construction of tetravalent, bispecific single-chain antibodies is taught, for example, in Coloma & Morrison, Nat. Biotechnol. 15, 159-63, 1997. Construction of bivalent, bispecific single-chain antibodies is taught in Mallender & Voss, J. Biol. Chem. 269, 199-206, 1994.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., Int. J Cancer 61, 497-501, 1995; Nicholls et al., J. Immunol. Meth. 165, 81-91, 1993).

Antibodies which specifically bind to a biomarker antigen also can be produced by inducing in vivo production in the lymphocyte population or by screening immunoglobulin libraries or panels of highly specific binding reagents as disclosed in the literature (Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies can be purified by methods well known in the art. For example, antibodies can be affinity purified by passage over a column to which the relevant antigen is bound. The bound antibodies can then be eluted from the column using a buffer with a high salt concentration.

Antibodies may be used in diagnostic assays to detect the presence or for quantification of the biomarkers in a biological sample. Such a diagnostic assay may comprise at least two steps; (i) contacting a biological sample with the antibody, wherein the sample is blood or plasma, a microchip (e.g., See Kraly et al. (2009) Anal Chim Acta 653(1): 23-35), or a chromatography column with bound biomarkers, etc.; and (ii) quantifying the antibody bound to the substrate. The method may additionally involve a preliminary step of attaching the antibody, either covalently, electrostatically, or reversibly, to a solid support, before subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); David et al., Biochem. 13:1014 (1974); Pain et al., J. Immunol. Methods 40:219 (1981); and Nygren, J. Histochem. and Cytochem. 30:407 (1982).

Immunoassays can be used to determine the presence or absence of a biomarker in a sample as well as the quantity of a biomarker in a sample. First, a test amount of a biomarker in a sample can be detected using the immunoassay methods described above. If a biomarker is present in the sample, it will form an antibody-biomarker complex with an antibody that specifically binds the biomarker under suitable incubation conditions, as described above. The amount of an antibody-biomarker complex can be determined by comparing to a standard. A standard can be, e.g., a known compound or another protein known to be present in a sample. As noted above, the test amount of a biomarker need not be measured in absolute units, as long as the unit of measurement can be compared to a control.

In various embodiments, biomarkers in a sample can be separated by high-resolution electrophoresis, e.g., one or two-dimensional gel electrophoresis. A fraction containing a biomarker can be isolated and further analyzed by gas phase ion spectrometry. Preferably, two-dimensional gel electrophoresis is used to generate a two-dimensional array of spots for the biomarkers. See, e.g., Jungblut and Thiede, Mass Spectr. Rev. 16:145-162 (1997).

Two-dimensional gel electrophoresis can be performed using methods known in the art. See, e.g., Deutscher ed., Methods In Enzymology vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in the one-dimensional array are further separated using a technique generally distinct from that used in the first separation step. For example, in the second dimension, biomarkers separated by isoelectric focusing are further resolved using a polyacrylamide gel by electrophoresis in the presence of sodium dodecyl sulfate (SDS-PAGE). SDS-PAGE allows further separation based on molecular mass. Typically, two-dimensional gel electrophoresis can separate chemically different biomarkers with molecular masses in the range from 1000-200,000 Da, even within complex mixtures.

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more biomarkers, the spot can be further analyzed by densitometric analysis or gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a biomarker can be analyzed by gas phase ion spectrometry. In gas phase ion spectrometry, the spots can be analyzed using any suitable techniques, such as MALDI or SELDI.

In a number of embodiments, high performance liquid chromatography (HPLC) can be used to separate a mixture of biomarkers in a sample based on their different physical properties, such as polarity, charge and size. HPLC instruments typically consist of a reservoir, the mobile phase, a pump, an injector, a separation column, and a detector. Biomarkers in a sample are separated by injecting an aliquot of the sample onto the column. Different biomarkers in the mixture pass through the column at different rates due to differences in their partitioning behavior between the mobile liquid phase and the stationary phase. A fraction that corresponds to the molecular weight and/or physical properties of one or more biomarkers can be collected. The fraction can then be analyzed by gas phase ion spectrometry to detect biomarkers.

After preparation, biomarkers in a sample are typically captured on a substrate for detection. Traditional substrates include antibody-coated 96-well plates or nitrocellulose membranes that are subsequently probed for the presence of biomarkers. Alternatively, metabolite-binding molecules attached to microspheres, microparticles, microbeads, beads, or other particles can be used for capture and detection of biomarkers. The metabolite-binding molecules may be antibodies, peptides, peptoids, aptamers, small molecule ligands or other metabolite-binding capture agents attached to the surface of particles. Each metabolite-binding molecule may comprise a "unique detectable label," which is uniquely coded such that it may be distinguished from other detectable labels attached to other metabolite-binding molecules to allow detection of biomarkers in multiplex assays. Examples include, but are not limited to, color-coded microspheres with known fluorescent light intensities (see e.g., microspheres with xMAP technology produced by Luminex (Austin, TX); microspheres containing quantum dot nanocrystals, for example, having different ratios and combinations of quantum dot colors (e.g., Qdot nanocrystals produced by Life Technologies (Carlsbad, CA); glass coated metal nanoparticles (see e.g., SERS nanotags produced by Nanoplex Technologies, Inc. (Mountain View, CA); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, CA); chemiluminescent dyes, combinations of dye compounds; and beads of detectably different sizes. See, e.g., U.S. Pat. Nos. 5,981,180, 7,445,844, 6,524,793, Rusling et al. (2010) Analyst 135(10): 2496-2511; Kingsmore (2006) Nat. Rev. Drug Discov. 5(4): 310-320, Proceedings Vol. 5705 Nanobiophotonics and Biomedical Applications II, Alexander N. Cartwright; Marek Osinski, Editors, pp. 114-122; Nanobiotechnology Protocols Methods in Molecular Biology, 2005, Volume 303; herein incorporated by reference in their entireties).

Mass spectrometry, and particularly SELDI mass spectrometry, is useful for detection of biomarkers. Laser desorption time-of-flight mass spectrometer can be used in various embodiments. In laser desorption mass spectrometry, a substrate or a probe comprising biomarkers is introduced into an inlet system. The biomarkers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry (MALDI-MS) can also be used for detecting biomarkers. MALDI-MS is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS, the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry.

Biomarkers on the substrate surface can be desorbed and ionized using gas phase ion spectrometry. Any suitable gas phase ion spectrometer can be used as long as it allows biomarkers on the substrate to be resolved. Preferably, gas phase ion spectrometers allow quantitation of biomarkers. In one embodiment, a gas phase ion spectrometer is a mass spectrometer. In a typical mass spectrometer, a substrate or a probe comprising biomarkers on its surface is introduced into an inlet system of the mass spectrometer. The biomarkers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of biomarkers or other substances will typically involve detection of signal intensity. This, in turn, can reflect the quantity and character of biomarkers bound to the substrate. Any of the components of a mass spectrometer (e.g., a desorption source, a mass analyzer, a detector, etc.) can be combined with other suitable components described herein or others known in the art.

The methods for detecting biomarkers in a sample have many applications. For example, the biomarkers are useful in monitoring women during pregnancy, for example to determine gestational age, predict time until delivery, or assess risk of spontaneous abortion.

Kits

In several embodiments, kits are utilized for monitoring women during pregnancy, wherein the kits can be used to detect analyte biomarkers as described herein. For example, the kits can be used to detect any one or more of the analyte biomarkers described herein, which can be used to determine gestational age, predict time until delivery, and/or assess risk of spontaneous abortion. The kit may include one or more agents for detection of one or more metabolite biomarkers, a container for holding a biological sample (e.g., blood or plasma) obtained from a subject; and printed instructions for reacting agents with the biological sample to detect the presence or amount of one or more biomarkers in the sample. The agents may be packaged in separate containers. The kit may further comprise one or more control reference samples and reagents for performing a biochemical assay, enzymatic assay, immunoassay, or chromatography. In various embodiments, a kit may include an antibody that specifically binds to a biomarker. In some embodiments, a kit may contain reagents for performing liquid chromatography (e.g., resin, solvent, and/or column).

A kit can include one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of monitoring women during pregnancy, e.g., to determine gestational age and/or predict time until delivery.

Applications and Treatments Related to Gestational Progress and Health

Various embodiments are directed to performing further diagnostics and/or treatments based on a determination of gestational progress. As described herein, a pregnant individual's gestational progress is determined by a computational model that incorporates temporally aligned analyte measurements. Based on one's gestational progress, an individual can be subjected to further diagnostic testing and/or treated with various medications, dietary supplements, and surgical procedures.

Clinical Diagnostics, Medications and Supplements

Several embodiments are directed to the use of medications and/or dietary supplements to treat an individual based on their gestational progress. In some embodiments, medications and/or dietary supplements are administered in a therapeutically effective amount as part of a course of treatment. As used in this context, to "treat" means to ameliorate at least one symptom of the disorder to be treated or to provide a beneficial physiological effect. For example, one such amelioration of a symptom could be improvement in gestational health. Assessment of gestational progress can be performed in many ways, including (but not limited to) the use of analyte measurements and sonography.

A therapeutically effective amount can be an amount sufficient to prevent reduce, ameliorate or eliminate the symptoms of diseases or pathological conditions susceptible to such treatment, such as, for example, spontaneous abortion or other gestational disorders. In some embodiments, a therapeutically effective amount is an amount sufficient to improve gestational health.

Various embodiments are directed towards getting an indication of gestational progress and performing an intervention and/or treatment thereupon. In some embodiments, when a pregnant individual is experiencing various symptoms at various points of gestational age or timeline to pregnancy (as determined by methods described herein), an intervention and/or treatment is performed. In some embodiments, treatments are performed when an individual exhibits symptoms that occur early and/or late according a determined gestational age or timeline to delivery. For example, a pregnant individual experiencing regular contractions prior to 37 weeks is considered to be in premature (preterm) labor, and a number of interventions and/or treatments can be performed. Likewise, gestation periods of longer than 42 weeks is considered to be a postterm pregnancy, additional monitoring, induction of labor, and/or Caesarian delivery is performed to avoid complications.

In a number of embodiments, when a pregnant individual is experiencing regular contractions, a gestational age can be determined, which would indicate whether the individual is experiencing preterm labor. In some embodiments, a gestational age is determined prior to any experienced contractions (e.g., as determined during the course of pregnancy) and based on the determined gestational age, an indication of preterm labor is determined. In accordance with various embodiments, it may be desirable to confirm that an individual is in preterm labor, and thus confirmation of labor can be performed by a number of means, including (but not limited to) cervical exam, sonography, testing for amniotic fluid, testing for fetal fibronectin, or any combination thereof. Treatments for preterm labor include (but not limited to) intravenous fluids, antibiotics (to treat infection), tocolytic medications (to slow or stop contractions), antenatal corticosteroids (to help mature fetus), cervical cerclage (to close up cervix), delivery of the baby, or any appropriate combination thereof. Tocolytic medications include (but not limited to) indomethacin, magnesium sulfate, orciprenaline, ritodrine, terbutaline, salbutamol, nifedipine, fenoterol, nylidrin, isoxsuprine, hexoprenaline, and atosiban. Antenatal corticosteroids include (but not limited to) dexamethasone and betamethasone. For more on treatment and care of preterm labor, see J. N. Robinson and E. R. Norwitz. Ed.: V. A. Barss. *UpToDate*, retrieved September 2019 (https:// www.uptodate.com/contents/preterm-birth-risk-factors-interventions-for-risk-reduction-and-maternal-prognosis); C. J. Lockwood. Ed.: V. A. Barss. *UpToDate*, retrieved September 2019 (https://www.uptodate.com/contents/preterm-labor-clinical-findings-diagnostic-evaluation-and-initial-treatment); and H. N. Simhan and S. Caritis. Ed.: V. A. Barss. *UpToDate*, retrieved September 2019 (https://www.uptodate.com/contents/inhibition-of-acute-preterm-labor); the disclosure of which are each incorporated herein by reference).

In several embodiments, a pregnancy may go beyond a gestational age of 42 weeks, as determined by various methods described herein. As gestational age exceeds 42 weeks, the placenta may age, begin deteriorating, or fail. Accordingly, a number of embodiments are directed towards determining a gestational age and determine whether the individual is in a postterm pregnancy. In some embodiments, when a postterm pregnancy is indicated, additional monitoring can be performed, including (but not limited to) fetal movement recording (to monitor regular movements of fetus), doppler fetal monitor (to measure fetal heart rate), nonstress test (to monitor fetal heartbeat) and Doppler flow study (to monitor blood flow in and out of placenta). In some embodiments, when a postterm pregnancy is indicated, labor is induced and/or Caesarian delivery is performed.

In many embodiments, the gestational age and time to delivery are determined and used concurrently to determine whether an individual will experience preterm labor or a postterm pregnancy. In some embodiments, a time to delivery equal to or less than a gestational age of 37 weeks is determined, indicating that preterm labor is likely and thus interventions and treatments for preterm labor are performed. Likewise, in some embodiments, a time to delivery equal to or more than a gestational age of 42 weeks is determined, indicating that a postterm pregnancy is likely and thus monitoring, induced labor, or Caesarian delivery are performed.

In a similar manner, interventions and/or treatments can be performed at various other time points, as would be understood in the art. Accordingly, various methods described herein can determine gestational progress and based on symptoms, can perform an intervention and/or a treatment. Critical time points include gestational ages of 20 weeks for determination of successful pregnancy and mitigating miscarriage, 24 weeks for determination age of viability, 28 weeks for determination of extreme preterm labor, 32 weeks for very preterm labor, 37 weeks for preterm labor, and 42 weeks for postterm pregnancy. At each time point, various interventions include prenatal checkups and monitoring, including measuring blood pressure, checking for urinary tract infection, checking for signs of preeclampsia, checking for signs of gestational hypertension, checking for signs of gestational diabetes, checking for signs of preterm labor, checking for signs of preterm rupture of membranes, measure heartbeat of fetus, measure fundal height, look for swelling in hands or feet, sampling for chorionic villus, check for risk of genetic disorders (e.g., Down syndrome and spina bifida), perform amniocentesis test, sonography, determine baby gender, and performing blood tests (e.g., glucose screening, anemia, status of Rh-positive or -negative).

EXEMPLARY EMBODIMENTS

Bioinformatic and biological data support the methods and systems of assessing gestational progress and applications utilizing computational models trained with temporally aligned data thereof. Exemplary methods and exemplary applications related to gestation that incorporate methods to temporally align analyte data features to build computational models are provided. Further, the predictive ability of the various models is described.

Precise determination of gestational age and time to delivery is critical in prenatal clinical care. Liang et al. introduce biomarkers using blood metabolites as an accessible and potentially more accurate alternative to current clinical practice determined by last menstruation date or ultrasound imaging (L. Liang, et al., Cell. 2020; 181:1680-1692, the disclosure of which is incorporated herein by reference). The data in Liang et al. was utilized to build supervised learning models for better performance, improving mean absolute prediction error in gestational age to potentially less than a week. Alignment of successive predictions for a single individual was found to improve overall accuracy, and thus this alignment is utilized within a longitudinal predictive model using principal curves. These methods may be applied to other situations where the outcome of interest is the time to or since an event, and multiple predictions are made at different times.

Accurate prediction of gestational age and time to delivery is essential for decision-making during pregnancy, including determination of pre-term birth and other treatments. To determine gestational age and due date, current clinical practice depends on information about the last menstruation date which may be unreliable, or ultrasound imaging which depends on accessibility in the early stages of pregnancy, and missing the time window is common even in developed countries. Accessible methods for prediction of gestational age and due date are hence needed.

Liang et al. (cited supra) introduced the potential use of blood metabolites as an affordable non-invasive method to predict gestational age and time to delivery. The current work expands on the preliminary analysis of data collected in the study and uses supervised learning methods to build predictive models for gestational age. Since the true gestational age is unknown, the learning models are trained on gestational age as estimated by the first trimester ultrasound, which is the current clinical gold standard. The work has resulted in an improvement of predictive performance on an independent validation cohort from a Mean Absolute Error (MAE) of 2.11 weeks (Root Mean-Squared Error, RMSE of 2.76 weeks) in Liang et al. to an MAE of 0.83 weeks (RMSE of 1.18 weeks). Models were also built to predict weeks to delivery for pregnant women.

Figures 4, 5:
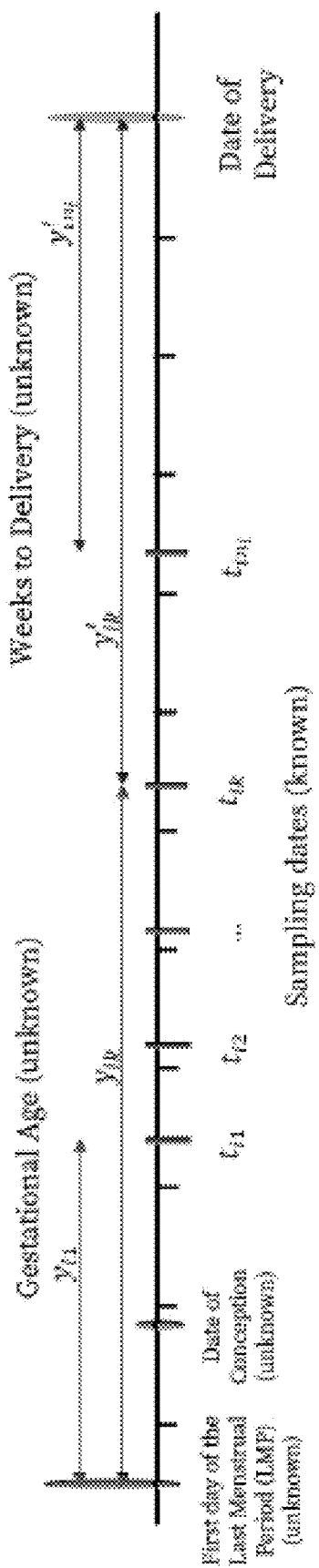
FIG. 4 provides a schematic of a timeline to compute gestational age or weeks to delivery utilizing several sampling dates in accordance with various embodiments.
FIG. 5 provides a table summarizing the demographics and birth characteristics of discovery and validation cohorts utilized to train and assess a computational model to determine gestational age or weeks to delivery, utilized in accordance with various embodiments.

This example uses multiple observations for a single patient to improve performance as compared to a model that does not take this into account. The model aligns the multiple predictions for a single individual in time, using the difference in the sampling times, which is also the difference in the response of interest (FIG. 4). This improves the predictions from a standard model such as boosted trees substantially. The model further improves performance by developing an approach inspired by this alignment, using principal curves (T. Hastie and W. Stuetzle Journal of the American Statistical Association, 1989; 84:502-516, the disclosure of which is herein incorporated by reference) where we fit observations at multiple times together.

For completeness, the data utilized in Liang et al. was utilized in the current example (FIG. 5). A multi-year, single-center Danish normal pregnancy cohort was established with a design for high-density blood sampling. Consenting female participants submitted weekly blood draws beginning in week 5 of pregnancy and ending in the postpartum period. A total of 30 women with weekly blood samples were assigned to a discovery (N=21) and a validation (N=9) cohort. The samples were analyzed in two separate years (see Liang et al., cited supra).

A total of 784 samples were collected from the 30 subjects. These were randomized, processed, and analyzed by liquid chromatography-mass spectrometry for untargeted metabolomics. 9,651 metabolic features across the different samples were identified after quality control, data filtering, and normalization. In addition, a subset of the metabolic features is also mapped to 264 chemical compounds. For more details about feature construction, see the Results section of Liang et al.

These pre-processed features of metabolites and chemical compounds were used as the input for analyses. In the study in Liang et al., samples are obtained from subjects at roughly weekly intervals, with the number of samples for a given subject ranging from 12 to 36. Generally, it is not expected for a pregnant individual to provide this high number of measurements in practice, and thus results were also generated with observations restricted to those closest to weeks 12, 16, and 26. These overlap with the windows for blood testing and glucose screening in current clinical practice.

For each of N pregnant women, there is a series of $n_i$ data pairs $(x_{ij}, y_{ij})$, $j=1, \ldots n_i$ $i=1, \ldots, N$. Each $x_{ij}$ is a vector of metabolic measurements which are used as features, and $y_{ij}$ is the response of interest, which is the gestational age as determined by ultrasound imaging. This can be replaced with $y'_{ij}$, the number of weeks to delivery (FIG. 4).

Because the timestamps $t_{ij}$ at which the samples are collected are known, for each individual, it can be assumed to $t_{i1}=0$, i.e. the $t_{ij}$ is interpreted as the time elapsed since the initial sampling time.

It is of interest to predict $y_{ij}$, given data available up to the current time. This includes $x_{ij}$, as well as prior measurements for the subject. Standard supervised learning methods predict $y_{ij}$ given $x_{ij}$. In the following, multiple observations are used for the same subject at different times, which improves performance over a standard model that does not take multiple observations into account.

Aligned Prediction Using Standard Supervised Learning

If one ignores the multiple observations and timestamps, various standard supervised learning method (such as LASSO, elastic net, and gradient boosted trees, etc.) could be utilized to build a model to predict the response $y_{ij}$, given $x_{ij}$ (see R. Tbshirani, Journal of the Royal Statistical Society: Series B (Methodological), 1996; 58:267-288; H. Zou and T. Hastie Journal of the royal statistical society: series B (statistical methodology), 2005; 67:301-320; and J. H. Friedman The Annals of Statistics, 2001; 29:1189-1232; the disclosure of which are each incorporated herein by reference). Better performance may be obtained, however, by using the temporal information to improve the predictions from one of these standard models.

For a given pregnant individual, let $y_{ij}$, $j=1, \ldots, n_i$ be the true response values at times $t_{ij}$, $j=1, \ldots, n$. Let $\hat{y}_{ij}$, $j=1, \ldots, n_i$ be the predictions from a standard model that uses $x_{ij}$ to predict $y_{ij}$.

Though the $y_{ij}$ are unknown, the differences can be determined:

$$y_{ij} - y_{ik}$$

which are equal to the differences in the sampling times $t_{ij}-t_{ik}$. At time $t_{ij}$, multiple estimators for $y_{ij}$ can be determined by offsetting other estimates for the same individual:

$$\hat{y}_{ij}, \hat{y}_{i(j-1)}+t_{ij}-t_{i(j-1)}, \ldots, \hat{y}_{i2}+t_{ij}-t_{i2}, \hat{y}_{i1}+t_{ij}-t_{i1}$$

These estimates can be combined to borrow strength across the different samples for a given pregnant individual. This results in a two-step procedure for prediction of $y_{ij}$, which averages the errors and potentially improves prediction accuracy:

Step 1. Use a standard supervised learning model to obtain predictions $\{\hat{y}_{ij}\}_{j=1}^{y b_s}$ Step 2. Align $\{\hat{y}_{ij}\}_{j=1}^{n_s}$ using the differences in times to produce aligned predictions $\{\tilde{y}_{ij}\}_{j=1}^{n_s}$, given by $$\tilde{y}_{ij} = \frac{1}{n_i}\sum_{k=1}^{n_i}(\hat{y}_{ik} + t_{ij} - t_{ik})$$

$$= t_{ij} + \frac{1}{n_i}\sum_{k=1}^{n_i}(\hat{y}_{ik} - t_{ik})$$

The $\{\tilde{y}_{ij}\}_{j=1}^{n_s}$, are aligned, i.e. $\tilde{y}_{ij}-\tilde{y}_{ik}=t_{ij}-t_{ik}$. This alignment can be performed for predictions from any model that produces estimates for $y_{ik}$. However, at any time, the model can only have access to measurements in the past. Hence, the alignment needs to be restricted to only observations and predictions that have already been made by that point.

For the data, it is observed that alignment of multiple observations improves performance on the validation set, as compared to standard supervised learning models that do not take multiple observations into account.

The alignment above provides a solution to the constrained optimization problem:

$$\underset{\{\tilde{y}_{ik}\}_{k=1}^{n_i}}{\text{minimise}} \sum_{k=1}^{n_i} (\tilde{y}_{ik} - \hat{y}_{ik})^2$$

s.t. $\tilde{y}_{ij} - \tilde{y}_{ik} = t_{ij} - t_{ik}$, $j, k = 1, \ldots, n_i$ in variables $\tilde{y}_{ij}$, $j=1, \ldots, n_i$.

Figure 6:
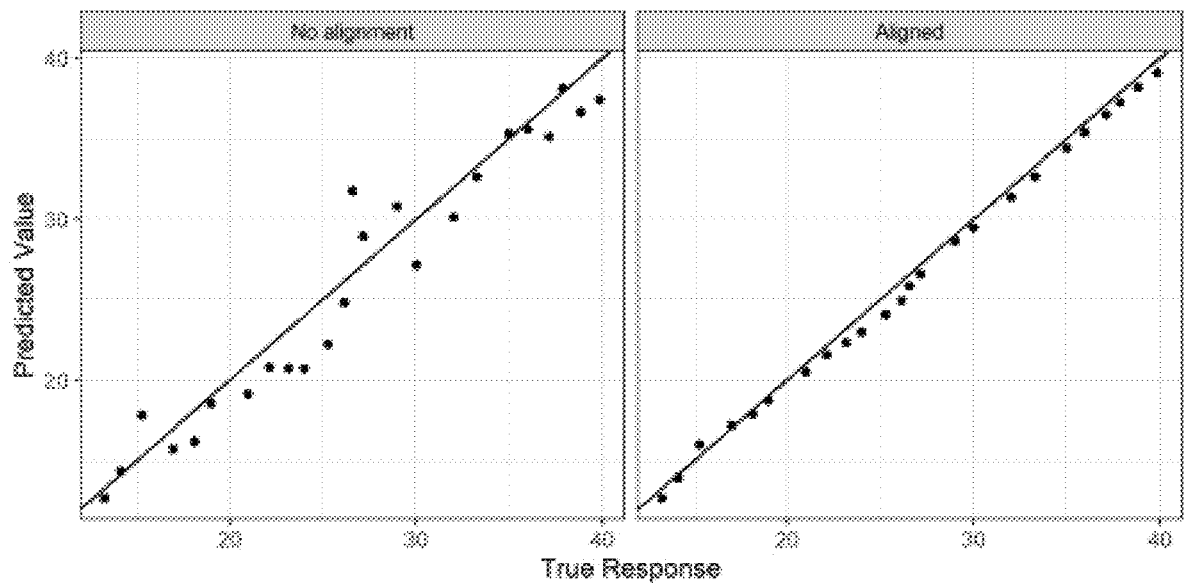
FIG. 6 provides an example of point predictions before and after alignment of a subject, the alignment performed using boosted trees, in accordance with various embodiments.

In other words, the $\tilde{y}_{ik}$ are chosen to minimize $L^2$ deviation from the original predictions while obeying the difference constraints. This may be extended to other loss functions as well. This optimization problem can be reformulated as $$\underset{\tilde{y}_{n_i}}{\text{minimise}} \sum_{k=1}^{n_i} (\hat{y}_{ik} - \tilde{y}_{in_i} - (t_k - t_{n_i}))^2$$

in the variable $\tilde{y}_{ni}$. An example of alignment results of point predictions for subject 26 of Liang et al is provided in FIG. 6.

Aligned Prediction Intervals

Alignment can be utilized to improve prediction intervals as well, through alignment of the left and right endpoints of the intervals respectively. For a given pregnant individual, let $y_{ij}$, $j=1, \ldots, i$ be the true response values and be the prediction intervals from any fixed model.

Let $\tilde{y}_k^l$, $j=1, \ldots, n_i$ be given by $$\tilde{y}_{ij}^l = \frac{1}{n_i}\sum_{k=1}^{n_i}(\hat{y}_{ik}^l + t_{ij} - t_{ik})$$

$$= t_{ij} + \frac{1}{n_i}\sum_{k=1}^{n_i}(\hat{y}_{ik}^l - t_{ik})$$

-continued $$\tilde{y}_{ij}^r = \frac{1}{n_i} \sum_{k=1}^{n_i} (\hat{y}_{ik}^r + t_{ij} - t_{ik})$$

$$= t_{ij} + \frac{1}{n_i} \sum_{k=1}^{n_i} (\hat{y}_{ik}^r - t_{ik})$$

Figure 7:
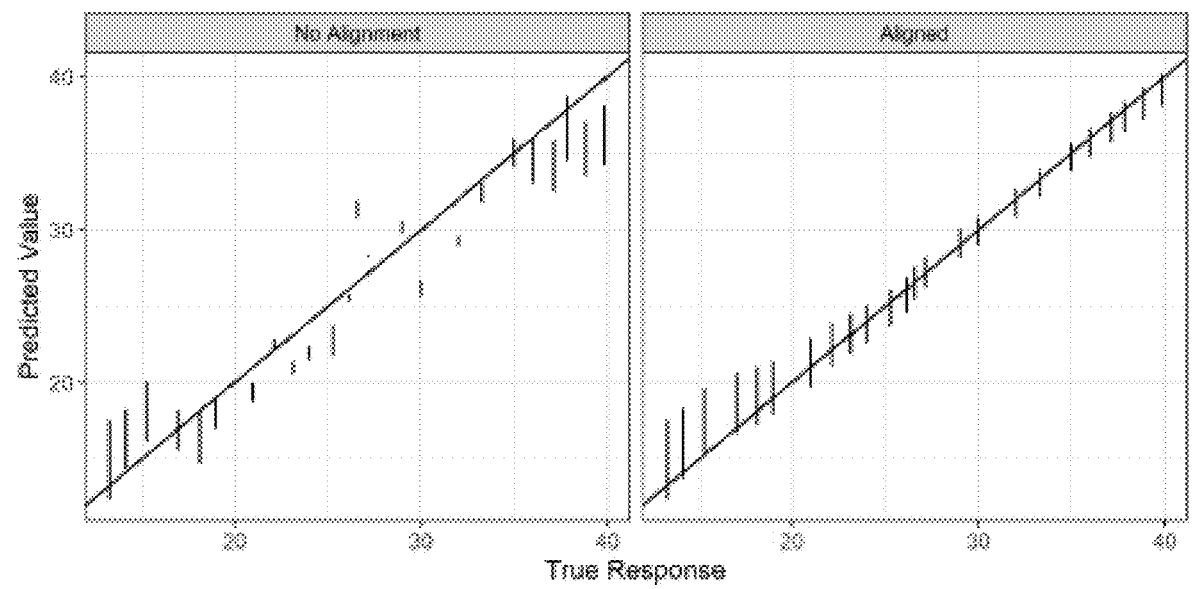
FIG. 7 provides an example of prediction intervals before and after alignment of a subject, the alignment performed using boosted trees, in accordance with various embodiments.

Then one can use $[\tilde{y}_{ij}^l, \tilde{y}_{ij}^u]$, j=1, . . . , $n_i$ as aligned prediction intervals in an analogous manner to point prediction. An example of alignment results of prediction intervals for subject 26 of Liang et al is provided in FIG. 7.

Aligned Prediction Using Principal Curve Approach

This section builds on the alignment results using principal curves (Hastie and Stuetzl, cited supra). The basic idea is to fit a one-dimensional curve in the feature space, as a function of time. This curve creates a mapping between the response y and the features $X \in \mathbb{R}^p$. This mapping can be used for prediction, using the points on the curve that are closest to the observed features. This method can take multiple observations into account and provide aligned predictions.

To obtain the curve, one can fit p separate functions $f_j(y)$, one per coordinate $X_j$ of X, each as a function of y over a specified domain A. For the gestational age data, assume A=[4, 42] weeks. Using the n=508 samples from N=21 subjects in the discovery cohort as the training set, each $f_j(y)$ is fit to the training data pairs $(X_j, y)$, pooling across all visits from all subjects in the training set. Specifically, a basis of natural splines in y is used, resulting in a one-dimensional curve f(y): $\mathcal{A} \mapsto \mathbb{R}^p$.

For a given subject, the predictions at the different sampling times are obtained by optimizing deviation from the one-dimensional curve at multiple points. These points are chosen using the difference in sampling times, and hence the predictions are naturally aligned.

The strategy for prediction is as follows:
1. Given a single observation $\chi_i \in \mathbb{R}^p$, estimate the response $y_i$ via $$\tilde{y}_i = \mathrm{argmin}_{y \in \mathcal{A}} \|\chi_i - f(y)\|^2$$

2. For a single subject, given observations $x_{i1}, \ldots, x \in \mathbb{R}^p$ RP at sampling times $t_{i1}, \ldots t_{in}$ (with to $t_{i1}=0$), estimate $y_{in}$ as $$\hat{y}_{in} = t_{in} + \mathrm{argmin}_{y \in \mathcal{A}} \sum_{k=1}^{n} \|x_{ik} - f(y + t_{ik})\|^2.$$

For the coordinate functions $f_j(y)$, it is ideal to have functions with distinguishing features that help in the prediction problem. It was observed that nonlinear functions were better than linear ones. Thus a basis of natural cubic splines was used to represent each of these functions. For the data, four interior knots at 10, 20, 30, and 40 and two boundary knots at 4 and 42 were used.

In very wide datasets, such as the full metabolite data in Liang et al., with p=9651, one would not expect all coordinates to be useful. In the training set, each coordinate function was screened using an F-test for the strength of the spline regression, and then threshold using a p-value for these regressions, selecting 100 features to be used for model fitting.

From the individual spline regressions for each of the selected features, the variance around the predicted curve was also recorded. Instead of using Euclidean distance in the distance calculations, each contribution was weight according to this variance:

$$\|x - f(y)\|_v^2 = \sum_{j=1}^{p} \frac{(x_j - f_j(y))^2}{v_j}.$$

Results: Gestational Age

The analysis in Liang et al. for prediction of gestational age (as determined by ultrasound) used a LASSO architecture and obtained a model with 42 features and an RMSE of 2.76 weeks for the validation set (N=9, n=245). This corresponds to an MAE of 2.11 weeks. As shown in the table of FIG. 8, the MAE was reduced to 0.83 and 1.13 weeks using the principal curve and boosted trees approaches, respectively. Thus, alignment clearly improves performance as compared to the previous models without alignment.

Prediction from all Visits and Full Feature Set

Figures 9, 10:
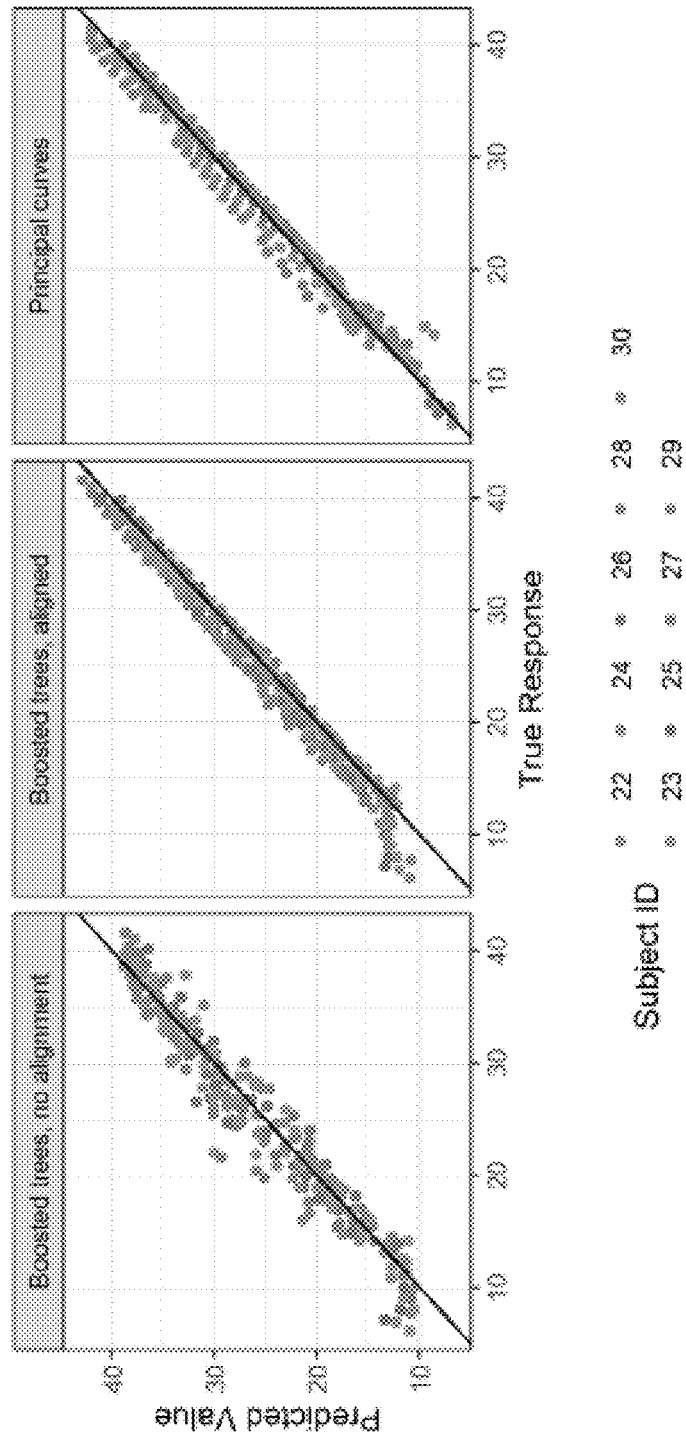
FIGS. 9 to 24 provide data tables and graphs depicting alignments and prediction of gestational age with various computational models using temporally aligned measurement data, generated in accordance with various embodiments.

The results from prediction of gestational age, using the full feature set and all visits, is provided in FIGS. 9 and 10 (n=245 samples from N=9 subjects in the validation set).

Figure 11:
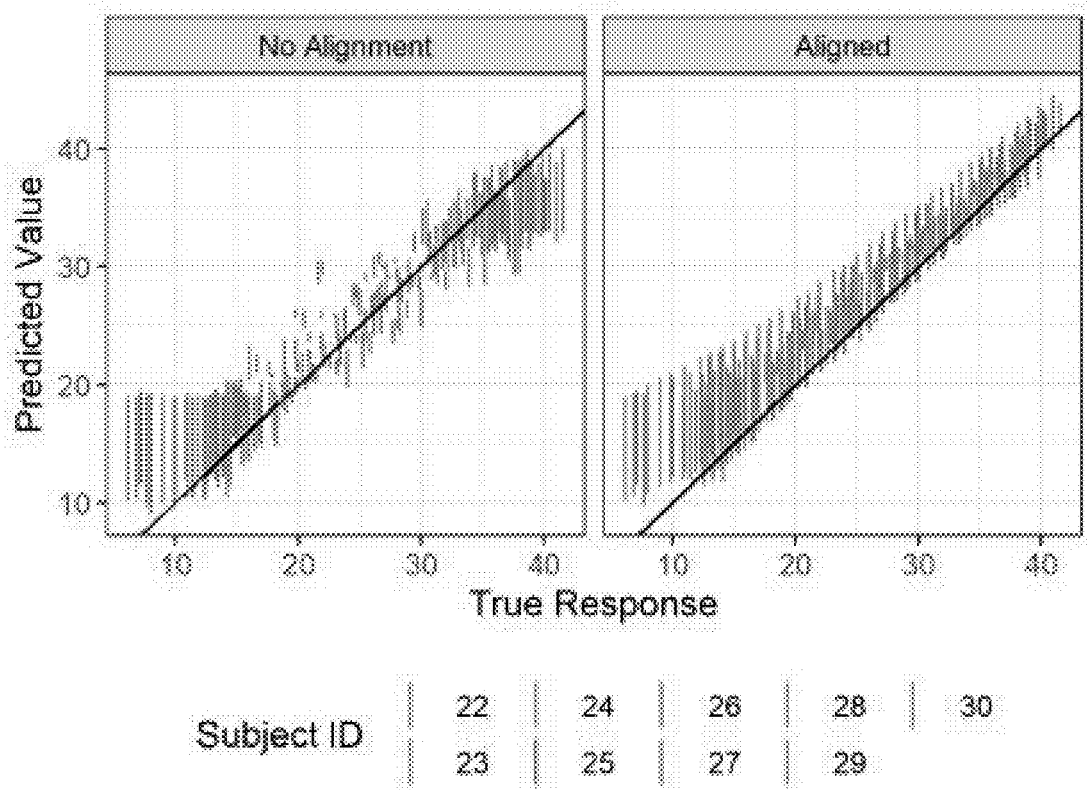
Figure 12:
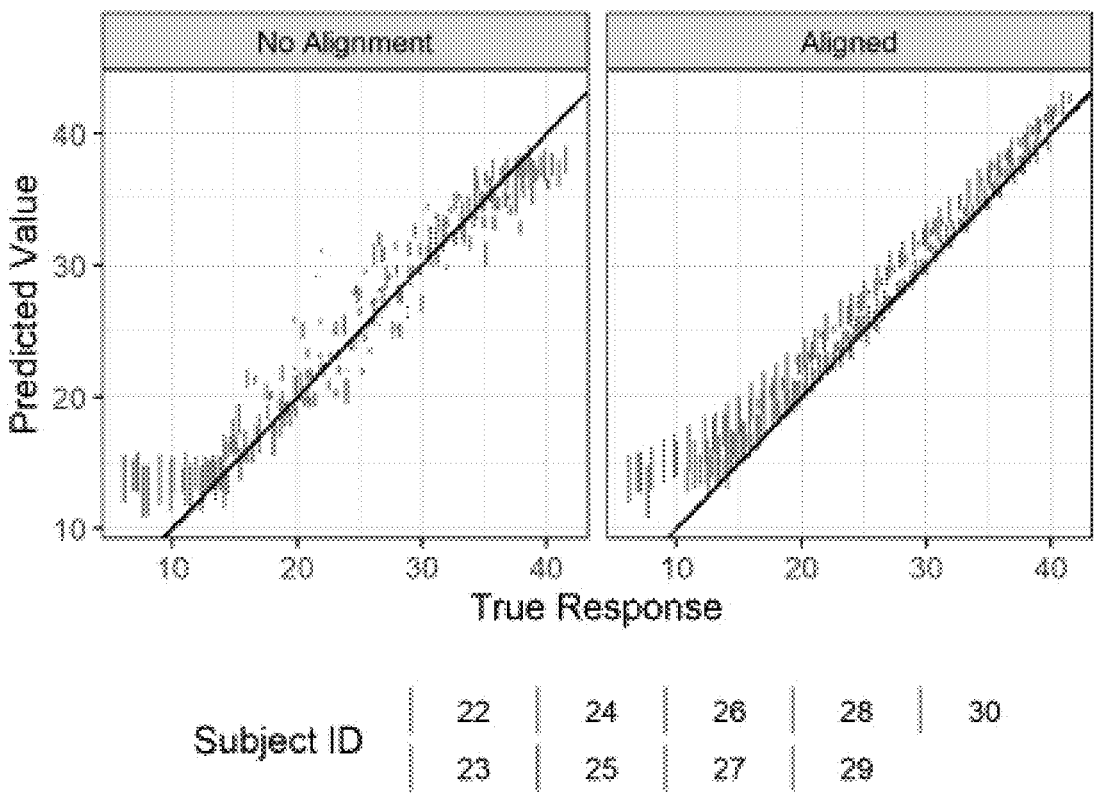

The plot of prediction intervals was developed as well, using quantile prediction with boosted trees (FIGS. 11 and 12). These intervals are wide, and more data may be required for better precision.

Figures 13, 14:
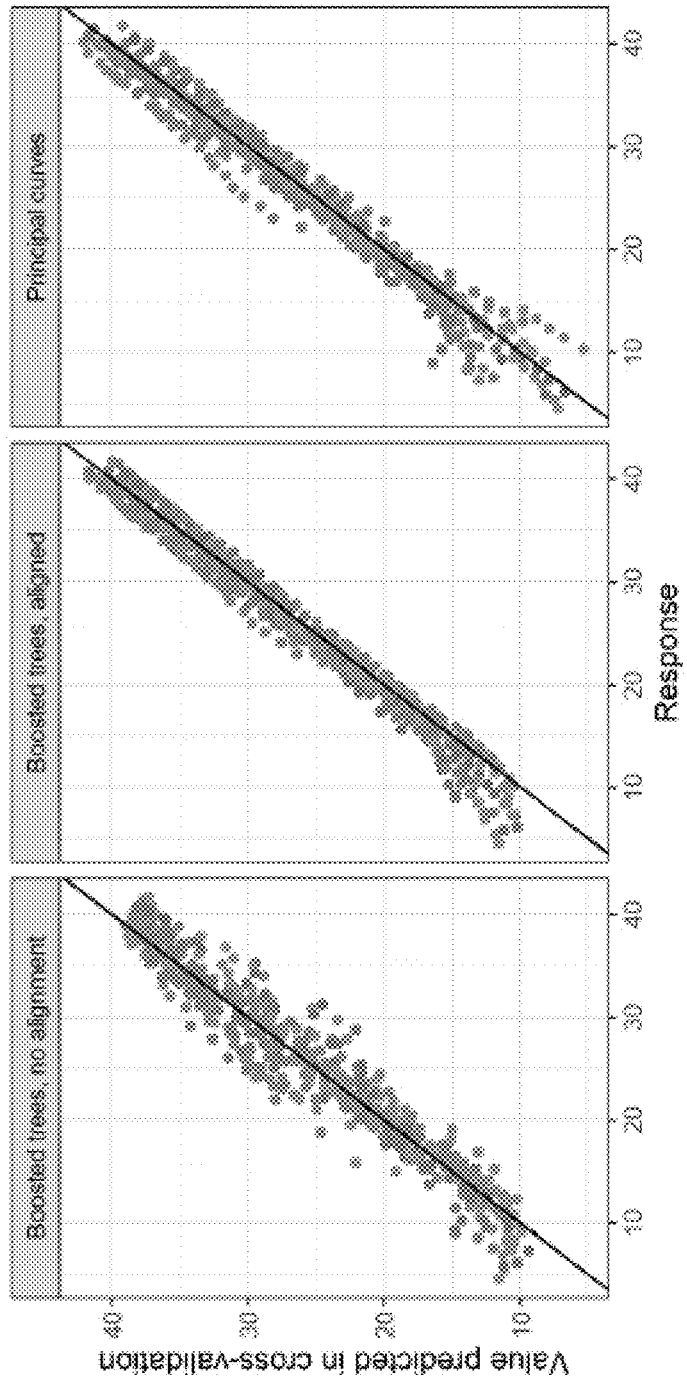

The results from 21-fold cross-validation, using the full feature set, and all visits, are provided in FIGS. 13 and 14. All samples from a given subject are in a single fold. A total n=508 samples from N=21 subjects were in the validation set.

Using a Reduced Feature Set

Figures 15, 16:
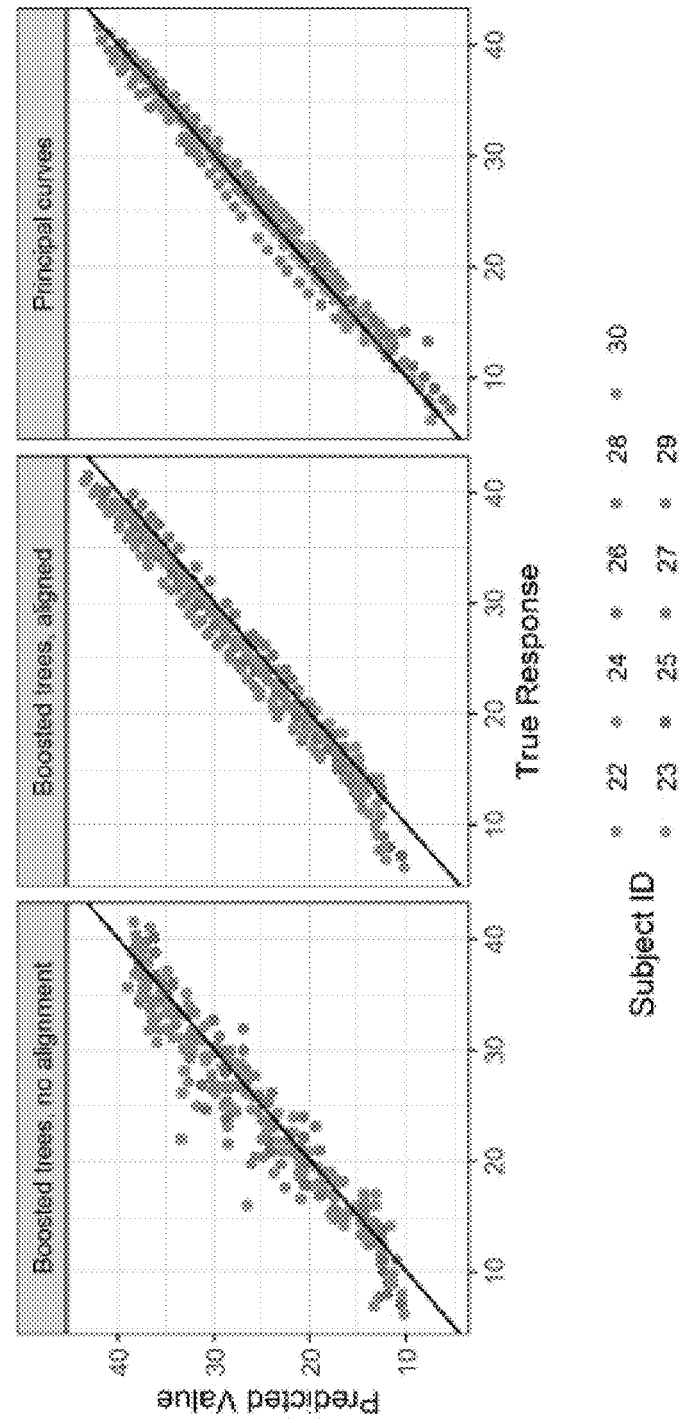

For potential clinical use, instead of the full feature set (p=9, 651), the annotated compounds were use as features for our prediction (p=264). It was observed that the principal curve approach performs remarkably well compared to models without any alignment of the predictions. The results, using the reduced set of features which are mapped to compounds and all visits, in FIGS. 15 and 16 (n=245 samples from N=9 subjects in the validation set).

Using a Smaller Set of Visits

Figures 17, 18:
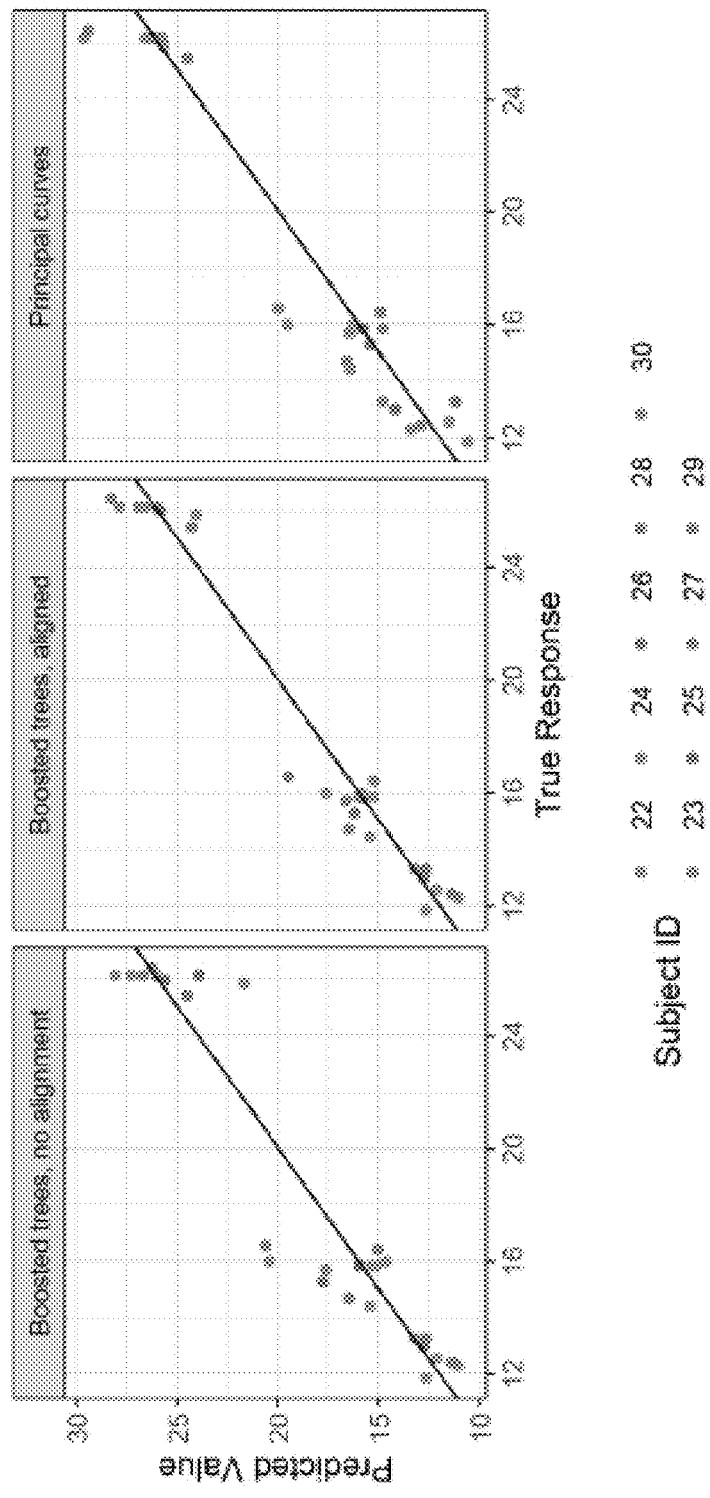

In practice, it may not be desirable to collect as many samples for each subject as were collected in the study. The validation set was restricted to only three visits for each subject, to get a total of N=9, n=27 observations. The three visits are chosen roughly around the 12th, 16th, and 26th weeks, which overlap with the windows for blood testing and glucose screening in current clinical practice. Around can be interpreted to mean within 2 weeks of the time point, or as is acceptable within clinical practice. The results from prediction of gestational age using the full feature set, and a maximum of three visits per subject, in FIGS. 17 and 18. We have a total n=27 samples from N=9 subjects in the validation set.

Figures 19, 20:
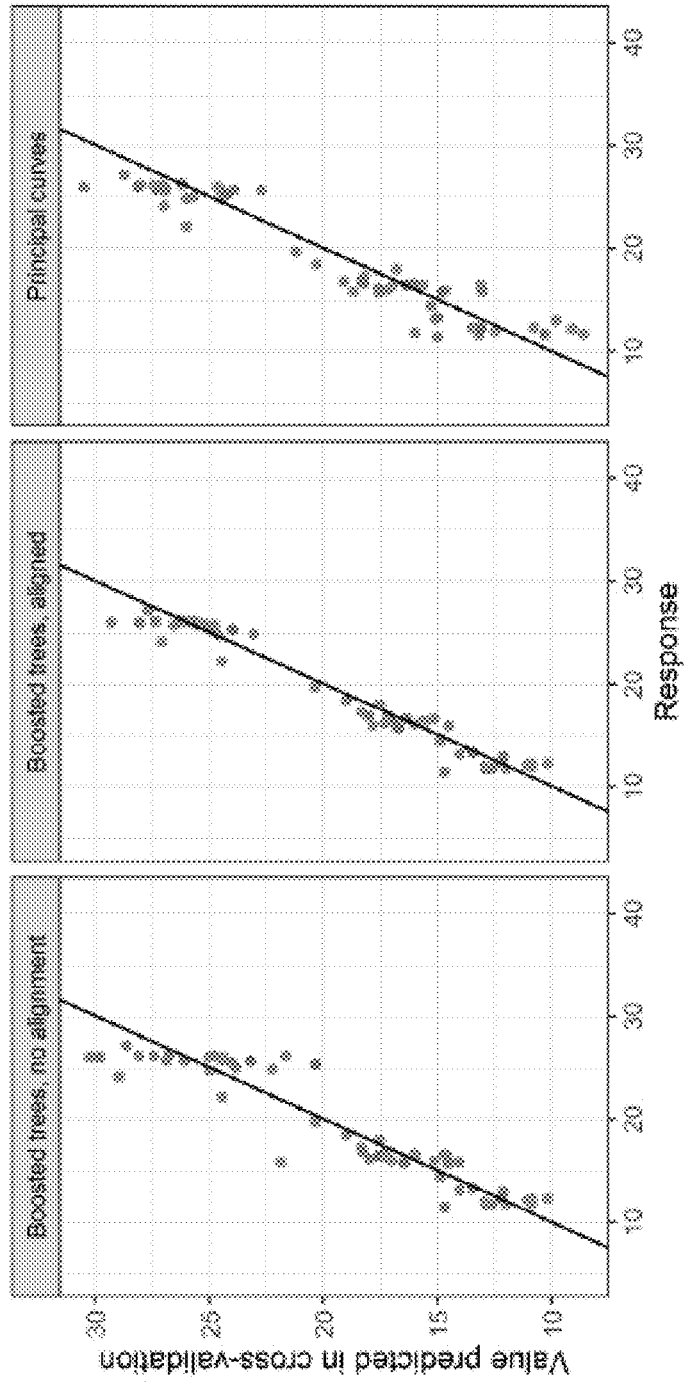

The results from 21-fold cross-validation, using the full feature set, and a maximum of 3 visits per subject, are provided in FIGS. 19 and 20. Folds were chosen such that each sample from each subject are in a single fold. A total of n=55 samples from N=21 subjects are in the validation set.

Figures 21, 22:
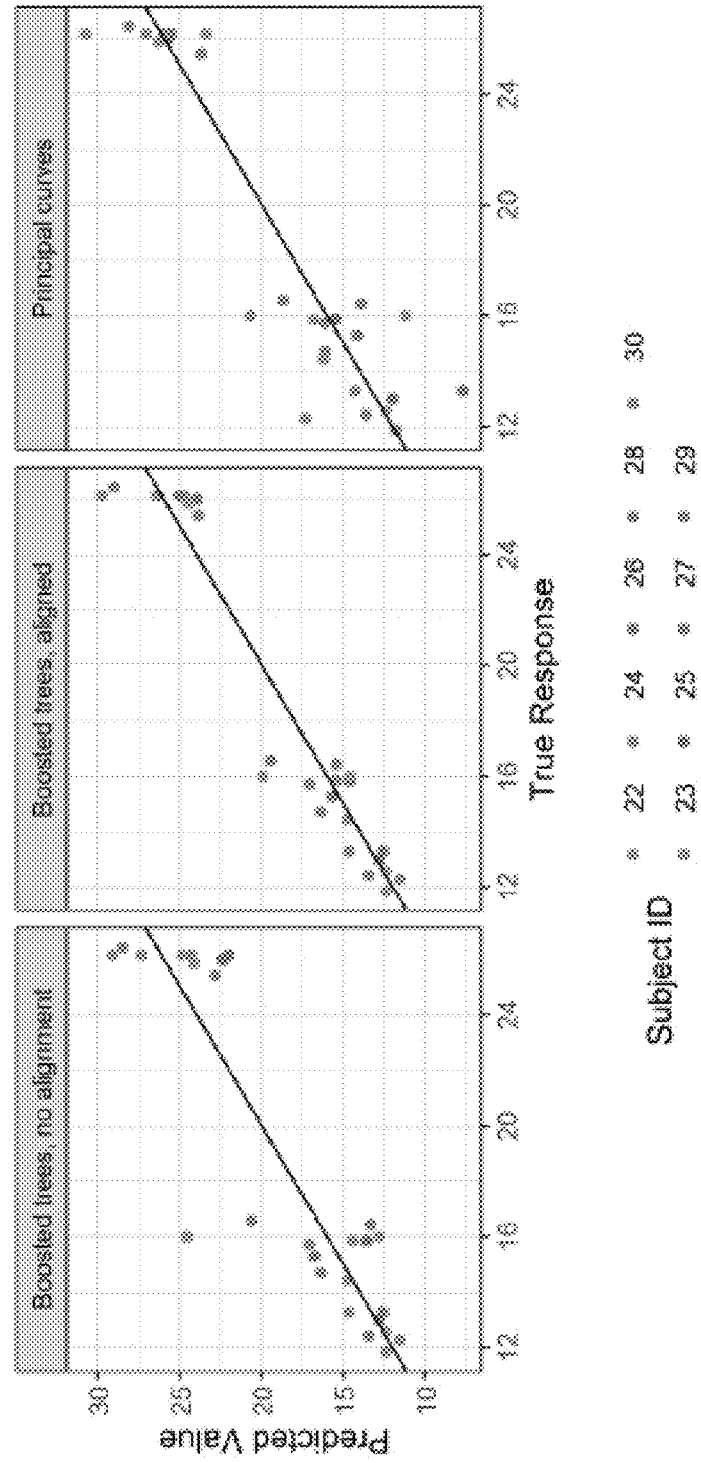

The results for predicting gestational age using the compounds data (p=264) with the restricted validation set, with only three visits per subject as well, is provided in FIGS. 21 and 22.

Figures 23, 24:
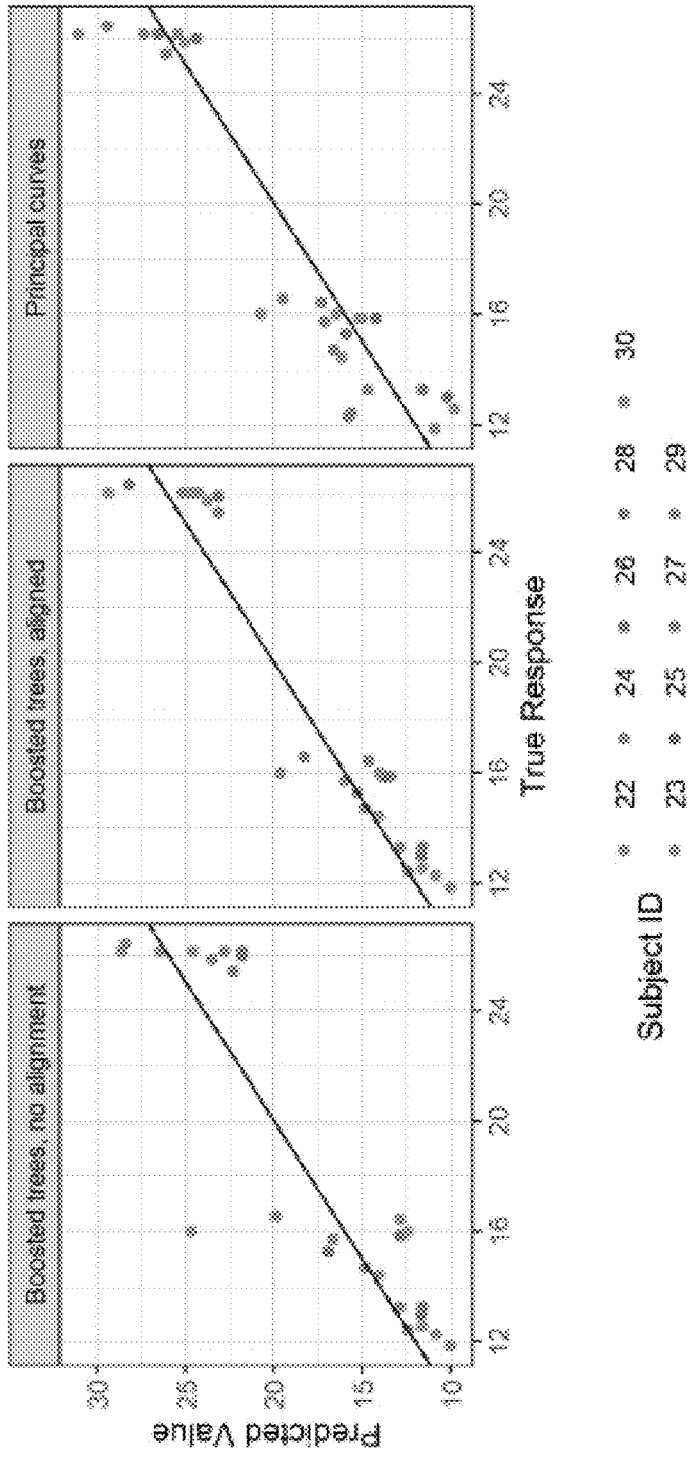

Performance was also measured using just a much smaller subset of features, which may be more feasible for utilizing within a clinical assay. The top three compounds, as determined by importance, were chosen in the boosted trees model for predicting gestational age. These compounds were Estriol-16-Glucuronide, THDOC, and Progesterone. The results for predicting gestational age using the top three compound data (p=3) with the restricted validation set, with only three visits per subject as well, is provided in FIGS. 23 and 24.

Results: Predicting Weeks to Delivery

As an addition, the time to delivery was also predicted for subjects. The alignment methods extend naturally to solve this problem as well. The data in the training and validation sets were limited to those subjects that had natural labor onsets, resulting with n=159 samples corresponding to N=6 subjects. A similar trend is observed across the different methods. The summary of the results is provided in the table of FIG. 25.

Figures 26, 27:
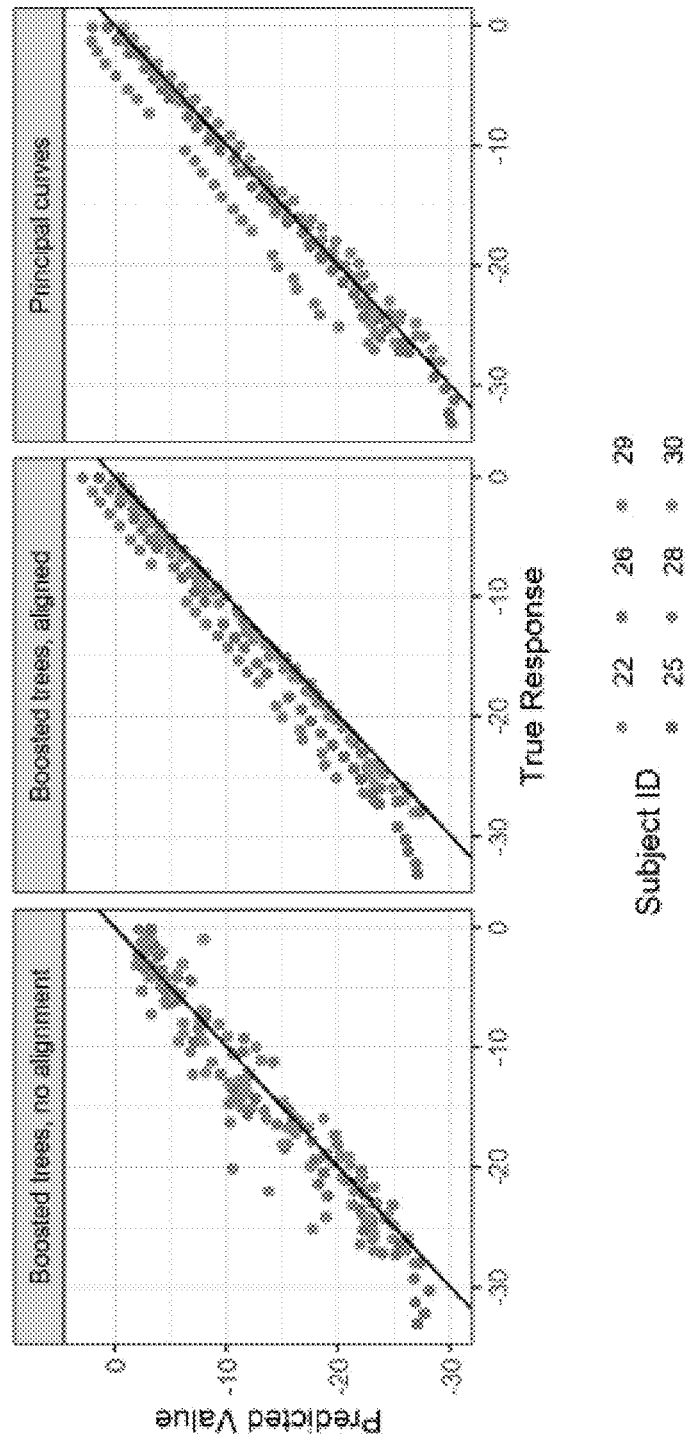
FIGS. 26 to 35 provide data tables and graphs depicting alignments and prediction of time to gestation with various computational models using temporally aligned measurement data, generated in accordance with various embodiments.

Results using the full dataset (n=159 samples from N=6 subjects; p=9, 651) are provided in FIGS. 26 and 27.

Figures 28, 29:
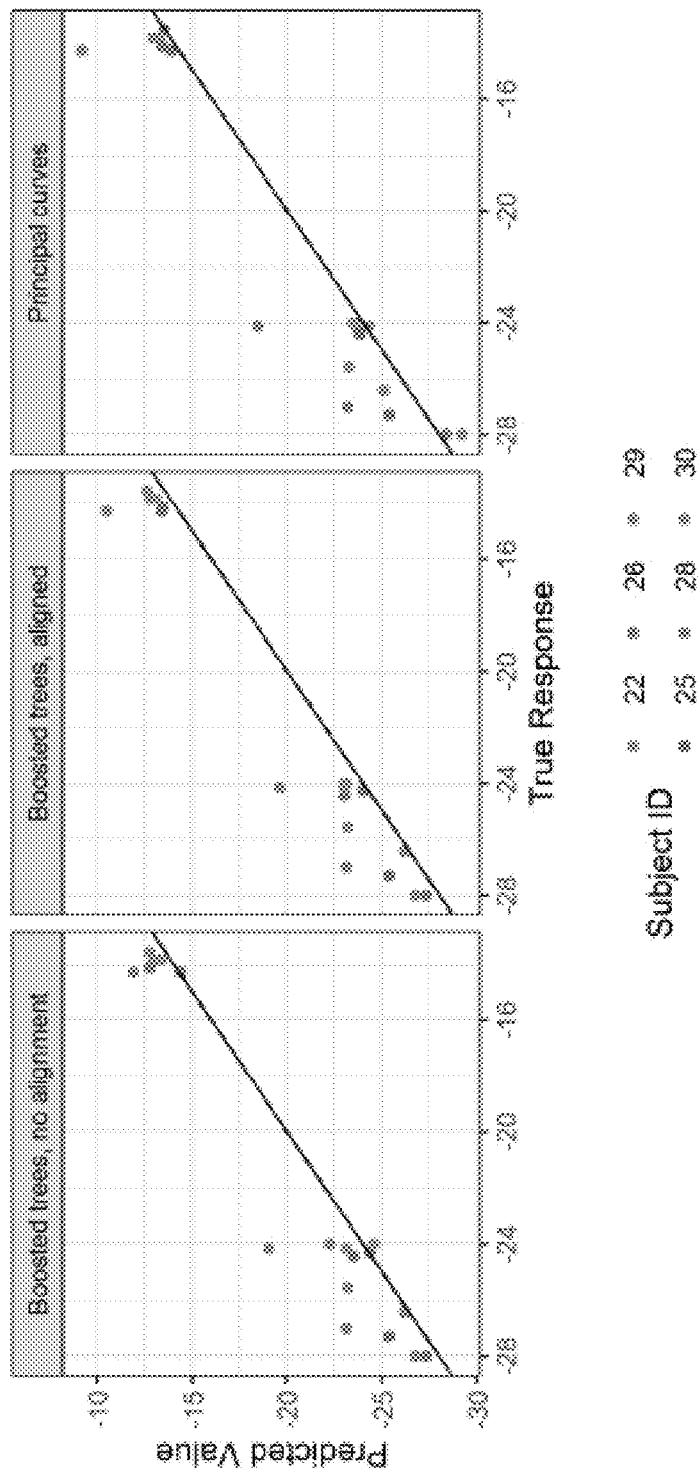

Results using only three visits per subject (n=18 samples from N=6 subjects; p=9, 651) are provided in FIGS. 28 and 29.

Figures 30, 31:
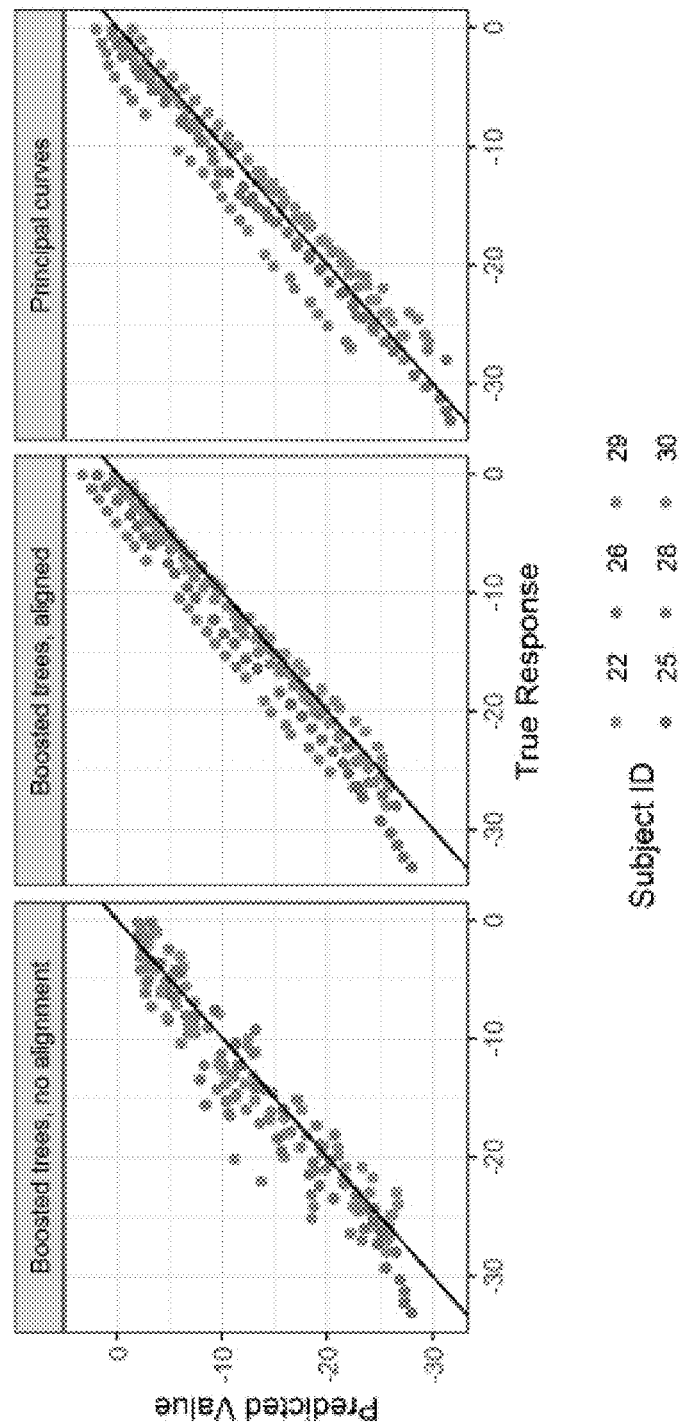

Results using just the compounds features (n=159 samples from N=6 subjects; p=264) are provided in FIGS. 30 and 31.

Figures 32, 33:
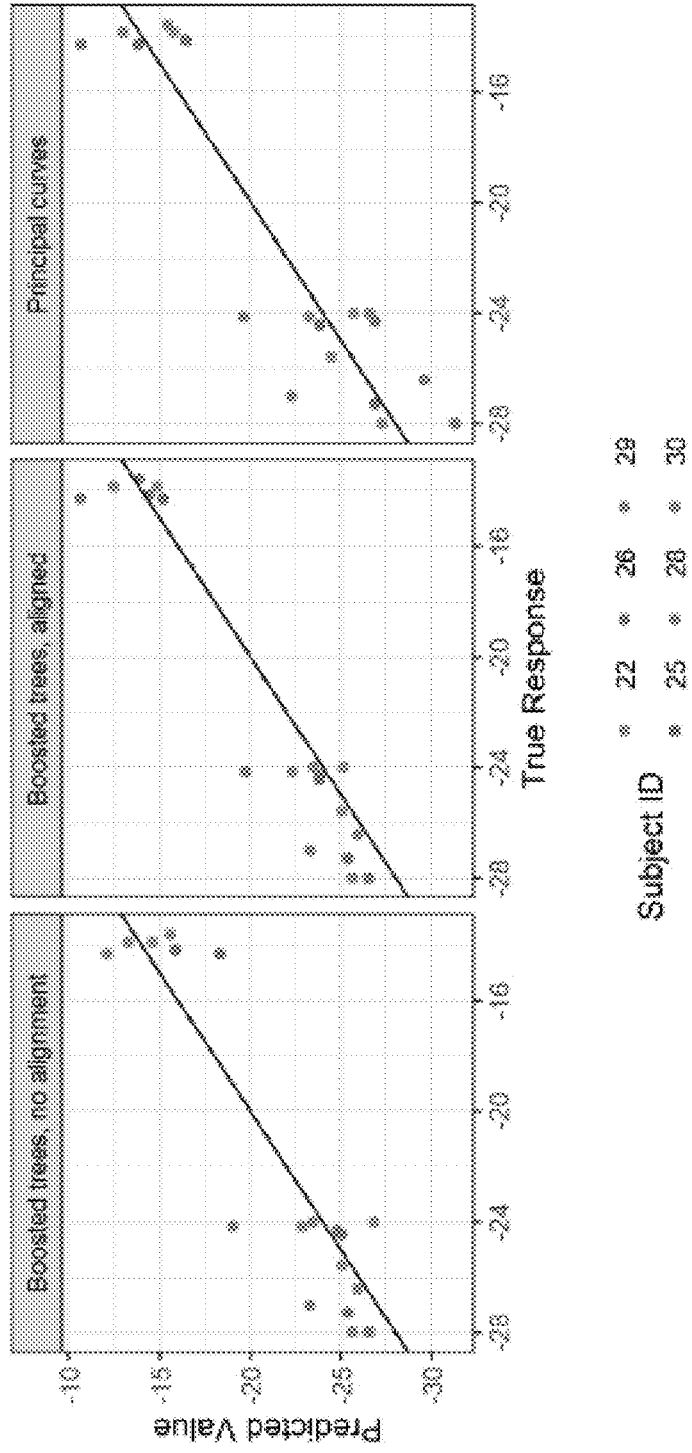

Results using just the compounds features, restricted to only three visits per subject, (n=118 samples from N=6 subjects; p=264) are provided in FIGS. 32 and 33.

Figures 34, 35:
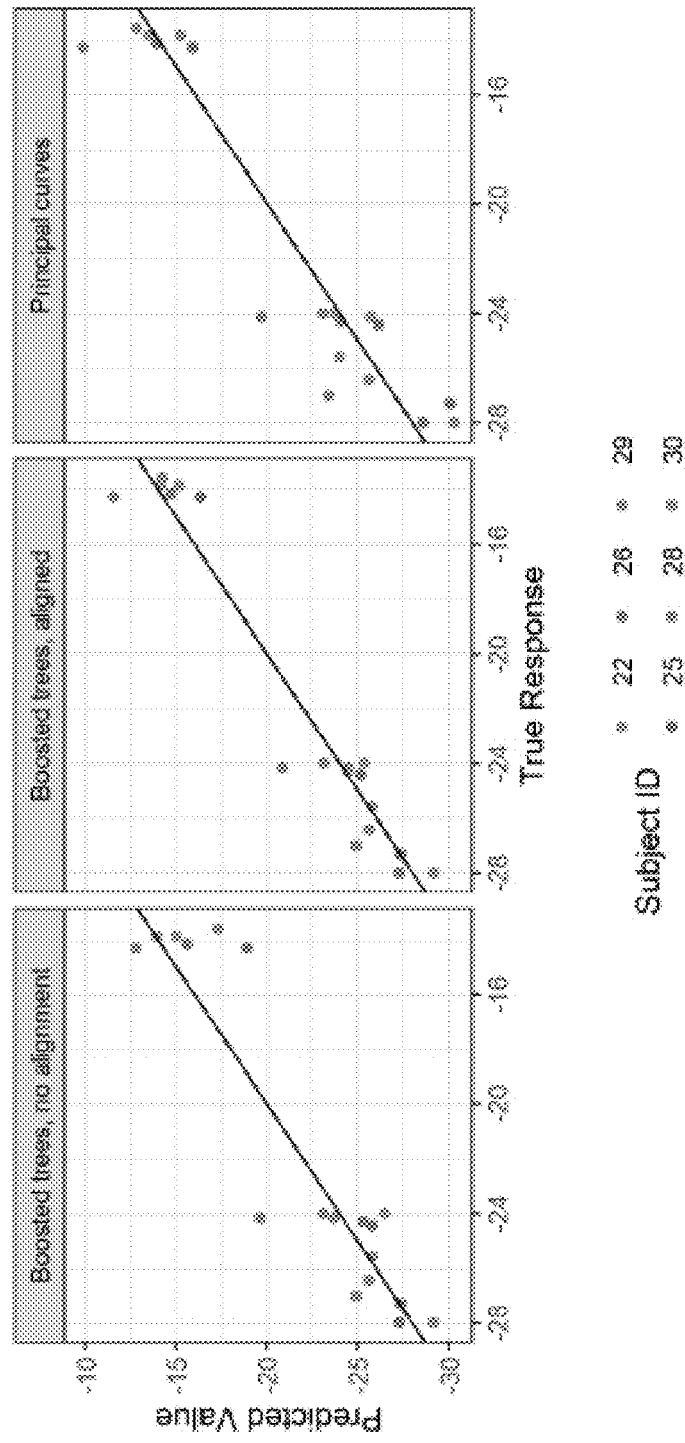

Results using only the top three markers Estriol-16 Glucuronide, THDOC, and Progesterone (n=18 samples from N=6 subjects; p=3) are provided in FIGS. 34 and 35.

CONCLUSIONS

Supervised learning methods were developed that use temporal information from multiple observations to improve predictive performance while predicting gestational age and weeks to delivery for pregnant human females. Multiple predictions were aligned from using differences in sampling times, which can be applied to any standard supervised learning method that does use this temporal aspect. This approached further utilized principal curves that provide aligned predictions. Using these methods, a better predictive performance was obtained on the data in Liang et al., reducing the Mean Absolute Error in predicting gestational age to less than a week.

These methods can be also applied to any problem in which the response of interest is a time to or from an event, and multiple predictions are made for a given observational unit at different time points, such as in survival analysis.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A method for determining gestational age or a time to delivery of an individual, the method comprising:
    collecting a biological sample of a pregnant individual from each time point of two or more time points;
    measuring one or more analytes of each of the two or more biological samples to yield a set of analyte measurements for each time point of collection; and
    determining a gestational age or a time to delivery of the pregnant individual via a computational model and the sets of analyte measurements, wherein each set of analyte measurements and its time point of collection are paired to yield a data feature that is utilized as input into the computational model;
    wherein the computational model has been trained utilizing temporally aligned data features provided by a cohort of pregnant individuals, and each data feature for training comprises a set of analyte measurements and its time point of collection, and each pregnant individual of the cohort utilized to train the model has provided two or more data features;
    wherein the computational model predicts the gestational age or the time to delivery of the pregnant individual using temporally aligned predictions of the pregnant individual and temporally aligned predictions of each pregnant individual within the training cohort, wherein each temporally aligned prediction is an error-corrected prediction that is corrected by temporal differences between the two or more data features.

2. The method according to claim 1, wherein the computational model comprises one of: ridge regression, K-nearest neighbors, LASSO regression, elastic net, least angle regression (LAR), random forest, boosted trees regression, or principal curves.

3. The method according to claim 1, wherein a feature in the model is a measurement of at least one of the following metabolites: N,N'-Dicarbobenzyloxy-L-ornithine, 1-(1Z-Hexadecenyl)-sn-glycero-3-phosphoethanolamine (PE(P-16:0e/0:0)), delta4-Dafachronic acid, C29H3609, 7alpha, 24-Dihydroxy-4-cholesten-3-one, C22H43012P, C27H4409, C19H2807S, Androstane-3,17-diol, 21-Hydroxypregnenolone, Estriol-16-Glucuronide, C25H4009, C27H4404, C27H4203, bilobol, [1-(3,5-dihydroxyphenyl)-12-hydroxytridecan-2-yl] acetate, C26H52NO8P, C27H4208, Prolylphenylalanine, N, N, Diacetyl-Lys-DAla-DAla, C23H49N205P, C21H290, C33H5309, C22H3503, C30H44NO3S, 1,1'-(1,8-dioxo-1,8-octanediyl)bis[glycylglycine], C27H42010, 6-ketoestriol sulfate, DAH-3-Keto-4-en, progesterone (m/z: 315, RT/min: 9.3), progesterone (m/z 337, RT/min 9.3), metabolite (m/z: 511, RT/min: 5.4), metabolite (m/z: 519, RT/min: 8.6), metabolite (m/z: 563, RT/min: 6.6), metabolite (m/z: 353, RT/min: 7.9), metabolite (m/z: 487, RT/min: 6.6), metabolite (m/z: 319, RT/min: 2.6), metabolite (m/z: 821, RT/min: 9.1), metabolite (m/z: 653, RT/min: 9.3), metabolite (m/z: 798, RT/min: 8.5), metabolite (m/z: 260, RT/min: 9.8), and metabolite (m/z: 823, RT/min: 9.3).

4. The method of claim 1, wherein a feature in the model is a measurement of at least one of the following metabolites: THDOC, estriol-16-glucuronide, and progesterone.

5. The method of claim 1, wherein two features in the model are each a measurement of at least two of the following metabolites: THDOC, estriol-16-glucuronide, and progesterone.

6. The method of claim 1, wherein three features in the model are each a measurement of the following metabolites: THDOC, estriol-16-glucuronide, and progesterone.

7. The method of claim 1, wherein the two or more time points comprise two time points around the $12^{th}$, $16^{th}$, and $26^{th}$ weeks of pregnancy.

8. The method of claim 1, wherein the two or more time points comprise three time points around the 12$^{th}$, 16$^{th}$, and 26$^{th}$ weeks of pregnancy.

9. The method of claim 1, wherein the two or more time points comprises at least three time points, and wherein the set of analyte measurements comprises at least one analyte measurement derived from each time point of the at least three time points from each individual of the cohort of pregnant individuals.

10. The method of claim 9, wherein the at least three time points are between 12 and 36 weeks of pregnancy as determined by sonography.

11. The method of claim 9, wherein the at least three time points comprise three time points around the 12$^{th}$, 16$^{th}$, and 26$^{th}$ weeks of pregnancy as determined by sonography.

12. The method of claim 1, wherein the computational model utilizes a supervised learning model, wherein the supervised learning model is LASSO, elastic net, or gradient boosted trees.

13. The method of claim 12, wherein the aligned predictions are yielded by:
the supervised learning model yields a prediction at a time point of collection or at a time interval between two collections, and
on an individual basis, prior predictions are utilized to average error of a current prediction based on the prior predictions and temporal differences between time points of collection.

14. The method of claim 1, wherein the computational model utilizes a principal curves model to yield a one-dimensional curve as function of time to map the data features based on time point of collection, wherein predictions of each pregnant individual are yielded by the mapped data features and deviation of the predictions is optimized based on where the data features are mapped on the one-dimensional curve.

15. The method of claim 1, further comprising performing further diagnostic testing based on the determined gestational age or the determined time to delivery.

16. The method of claim 1, further comprising treating the individual based on the determined gestational age or the determined time to delivery.

17. The method of claim 16, wherein the treatment is one of: a medication, a dietary supplement, a Caesarian delivery, or a surgical procedure.

* * * * *